(12) United States Patent
Matsuura

(10) Patent No.: US 9,927,433 B2
(45) Date of Patent: Mar. 27, 2018

(54) TEST APPARATUS

(71) Applicant: SHIN CORPORATION, Kobe-shi, Hyogo (JP)

(72) Inventor: Shinji Matsuura, Kobe (JP)

(73) Assignee: SHIN CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 15/329,075

(22) PCT Filed: Aug. 17, 2015

(86) PCT No.: PCT/JP2015/073049
§ 371 (c)(1),
(2) Date: Jan. 25, 2017

(87) PCT Pub. No.: WO2016/027782
PCT Pub. Date: Feb. 25, 2016

(65) Prior Publication Data
US 2017/0227536 A1  Aug. 10, 2017

(30) Foreign Application Priority Data
Aug. 20, 2014  (JP) ................. 2014-167984

(51) Int. Cl.
*G01N 33/543*   (2006.01)
*G01N 1/40*     (2006.01)
(Continued)

(52) U.S. Cl.
CPC ......... *G01N 33/54366* (2013.01); *G01N 1/20* (2013.01); *G01N 1/4055* (2013.01);
(Continued)

(58) Field of Classification Search
CPC combination set(s) only.
See application file for complete search history.

(56) References Cited

U.S. PATENT DOCUMENTS 4,742,011 A * 5/1988 Blake ...................... B01L 3/502
                                                        422/412
5,225,163 A * 7/1993 Andrews ............ G01N 33/5302
                                                        422/413
(Continued)

FOREIGN PATENT DOCUMENTS

JP    2005-526954 A    9/2005
JP    2007-511767 A    5/2007
(Continued)

OTHER PUBLICATIONS

International Search Report dated Dec. 22, 2015, issued in counterpart application No. PCT/JP2015/073049. (2 pages).

*Primary Examiner* — Brian R Gordon
(74) *Attorney, Agent, or Firm* — Westerman, Hattori, Daniels & Adrian, LLP

(57) ABSTRACT

The test device is provided with a testing means for testing an added extraction solution utilizing immunochromatography or nucleic acid chromatography, an extraction solution container, and a tubular guiding member having an extraction solution inflow port communicating with the extraction container in a sealed manner at one end side and having an extraction solution outflow port at the other end side. The guiding member is configured so as to have inside the tube a rod-shaped extraction solution guide having capillary action and having one end at the extraction solution outflow port side able to contact the testing means and so that the extraction solution absorbed from the extraction solution inflow port side at the extraction solution guide moves by capillary action through the inside of the extraction solution guide and is added to the testing means through the one end of the extraction solution guide contacting the testing means.

11 Claims, 16 Drawing Sheets

(51) Int. Cl.
*G01N 33/558* (2006.01)
*G01N 1/20* (2006.01)
*G01N 1/10* (2006.01)

(52) U.S. Cl.
CPC ... *G01N 33/558* (2013.01); *G01N 2001/1025* (2013.01); *G01N 2001/4061* (2013.01)

(56) References Cited

U.S. PATENT DOCUMENTS

| | | | | |
|---|---|---|---|---|
| 5,658,531 A * | 8/1997 | Cope | | B01L 3/502 422/410 |
| 5,772,961 A * | 6/1998 | Mico | | B01L 3/5023 422/412 |
| 6,017,494 A * | 1/2000 | Ashihara | | B01L 3/5023 422/412 |
| 6,071,478 A * | 6/2000 | Chow | | B01L 3/502715 422/502 |
| 6,096,268 A * | 8/2000 | Inbar | | G01N 33/54366 422/412 |
| 6,565,808 B2 * | 5/2003 | Hudak | | B01L 3/5023 422/411 |
| 6,814,937 B1 * | 11/2004 | Hirota | | B01J 19/0046 347/20 |
| 6,827,831 B1 * | 12/2004 | Chow | | B01J 19/0093 204/450 |
| 6,919,045 B1 * | 7/2005 | Berndt | | B01J 19/0093 204/450 |
| 7,090,803 B1 * | 8/2006 | Gould | | B01L 3/5023 422/413 |
| 7,452,507 B2 * | 11/2008 | Renzi | | B01L 3/502715 204/452 |
| 7,674,615 B2 * | 3/2010 | Ramel | | B01L 3/5023 422/412 |
| 7,837,939 B2 * | 11/2010 | Tung | | A61B 10/0045 422/410 |
| 7,910,381 B2 * | 3/2011 | Ford | | G01N 33/558 422/422 |
| 8,007,626 B2 * | 8/2011 | Pattekar | | B01J 19/0093 156/293 |
| 8,454,892 B1 * | 6/2013 | Rychwalski | | G01N 33/1826 422/527 |
| 8,507,260 B2 * | 8/2013 | Alajem | | B01L 3/5023 422/400 |
| 8,673,239 B2 * | 3/2014 | Niedbala | | A61B 10/0045 422/430 |
| 8,795,607 B2 * | 8/2014 | Kurowski | | B01L 3/502715 137/68.23 |
| 8,986,527 B2 * | 3/2015 | Lin | | G01N 27/26 204/411 |
| 2003/0064526 A1 | 4/2003 | Niedbala et al. | | |
| 2003/0129767 A1 * | 7/2003 | Bautista | | B01L 3/5023 436/178 |
| 2004/0202581 A1 * | 10/2004 | Berndt | | B01J 19/0093 422/502 |
| 2005/0119589 A1 | 6/2005 | Tung et al. | | |
| 2005/0181521 A1 | 8/2005 | Niskanen et al. | | |
| 2005/0233466 A1 * | 10/2005 | Wright | | G01N 11/14 436/165 |
| 2010/0255609 A1 * | 10/2010 | Rutter | | B01L 3/5023 436/518 |
| 2014/0161686 A1 * | 6/2014 | Bort | | B01L 3/502715 422/502 |
| 2015/0343445 A1 * | 12/2015 | Bagnato | | B01F 15/0404 435/40.5 |

FOREIGN PATENT DOCUMENTS

| | | |
|---|---|---|
| JP | 2007-523337 A | 8/2007 |
| JP | 4801030 B2 | 10/2011 |
| JP | 2012-247231 A | 12/2012 |
| JP | 2013-228235 A | 11/2013 |

* cited by examiner

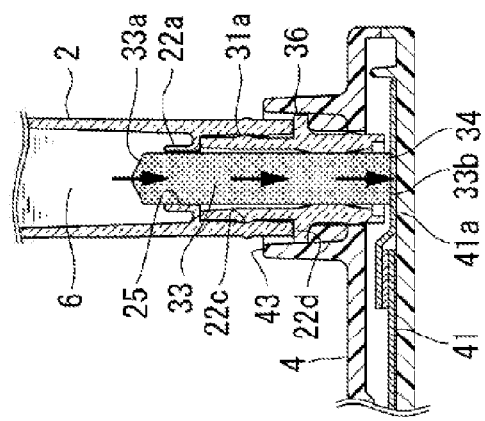
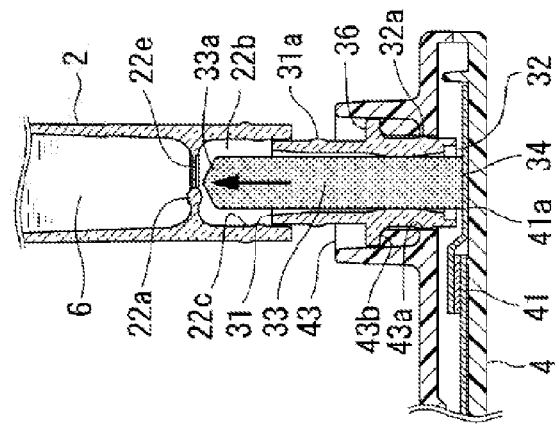
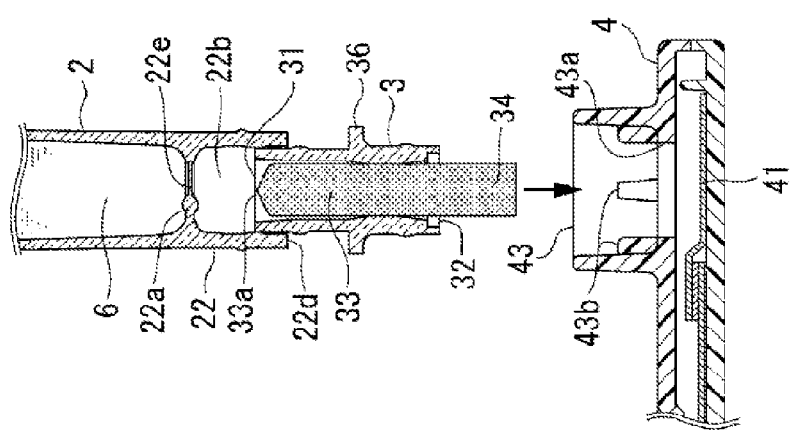

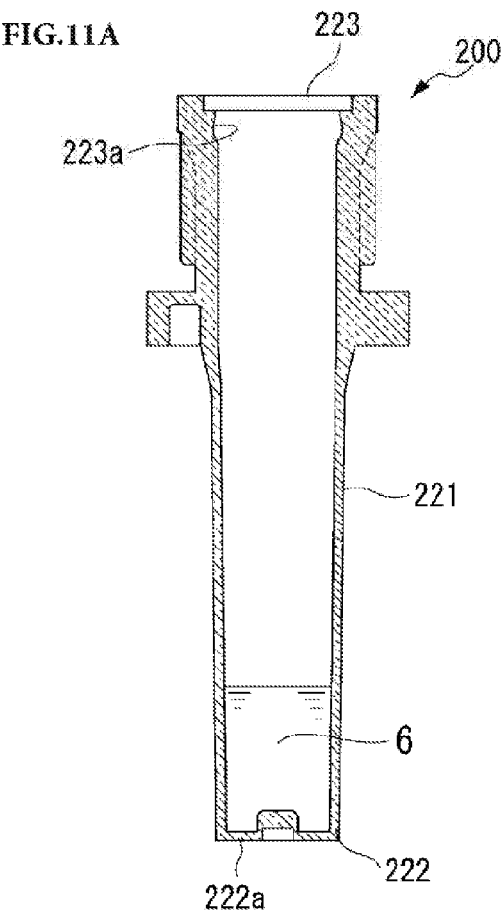
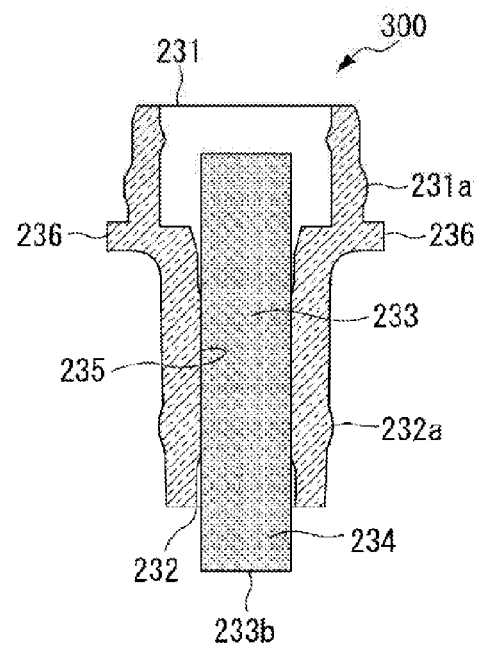
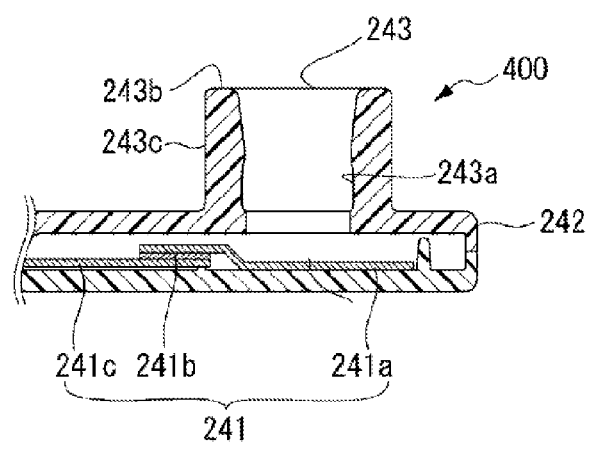
FIG.11A
FIG.11B
FIG.11C

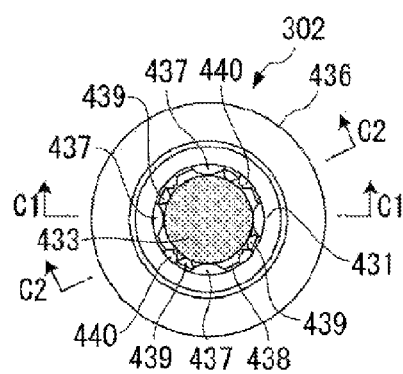
FIG.15A
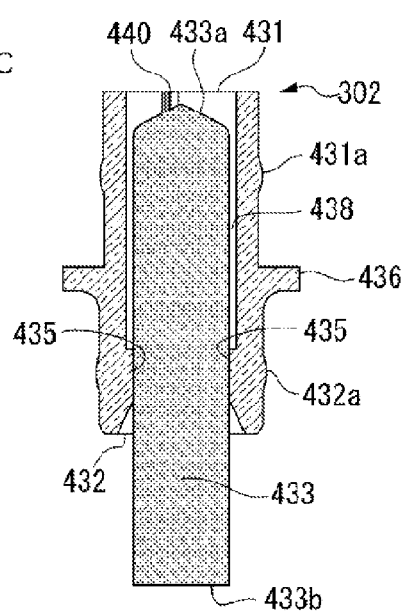
FIG.15B
FIG.15C
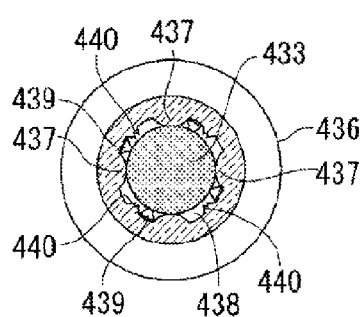
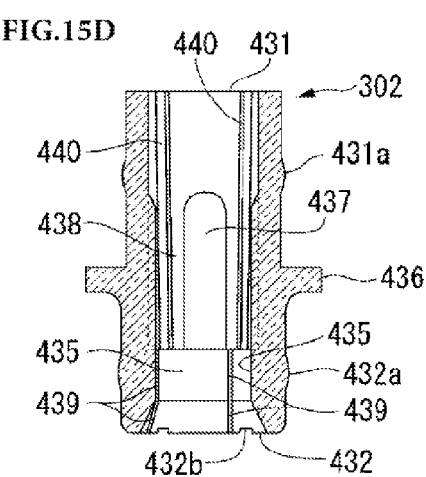
FIG.15D
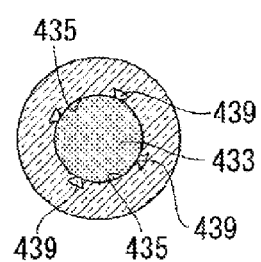
FIG.15E  FIG.15F

TEST APPARATUS

TECHNICAL FIELD

The present invention relates to a test device used for testing specimens such as swabs of the nasal cavity and throat, nasal discharge, sputum, urine, serum, feces, or rectal swabs. Specifically, it relates to a test device able to prevent infection or contamination by specimens and able to simply test specimens.

BACKGROUND ART

In recent years, in clinical tests for diagnosing the state of health of patients, clinical tests utilizing immunochromatography have often been used. Immunochromatography has the excellent features of (1) not requiring any special measurement machines and enabling visual determination, (2) enabling the tests to be completed in an extremely short time of several minutes or so, and (3) being simple in test operation and not requiring any special skill. Due to these features, immunochromatography is used mainly for testing for influenza and other viruses and testing for bacterial infection at medical facilities. It enables the quick start of treatment and accurate action after the test diagnosis.

The tests for viruses and the tests for bacterial infection by immunochromatography are mainly performed on specimens obtained by cotton swabs and other swabs and specimen samplers from the nasal cavities, throats, mucous membranes, etc. of patients. An obtained specimen is immersed in an extraction solution to be dispersed or dissolved to prepare a development solution for immunochromatography measurement. As shown in FIG. 18, the extraction solution 6' in which this specimen is dispersed is added dropwise in a predetermined amount from an addition hole 43' provided in the surface of a housing 42' in which an immunochromatography test strip 41' is inserted to thereby be introduced into the test strip 41'. At that time, if a highly contagious virus or bacteria etc. is contained in the specimen, the specimen extraction solution and the used specimen sampler are liable to infect a handler touching them, the specimen extraction solution is liable to splatter or leak to the outside environment, and the specimen sampler is liable to contact the outside environment etc. resulting in microbial contamination. For this reason, measures have to be taken against infection and microbial contamination not only during the tests, but until the specimen sampler and specimen extraction solution etc. are discarded after the test.

Therefore, the applicant has proposed test kits enabling prevention of contact with the handler and leakage etc. to the outside environment (PLT 1 and PLT 2).

The test kit proposed in PLT 1 is mainly provided with a specimen sampling part, a container inside of which a specimen extraction solution is held, and a sealing lid with a specimen sampler holding function for sealing an opening part of the container while the specimen sampler is held in the container. For this reason, this test kit can seal the specimen extraction solution and the used specimen sampler in the space formed by the container and the sealing lid with a specimen sampler holding function after moving the specimen sampled by the specimen sampler to the specimen extraction solution.

Further, the test kit proposed in PLT 2 is mainly provided with a specimen sampler provided with a specimen sampling part at one end in its longitudinal direction and with a cap part at the other end in its longitudinal direction and provided with a shaft part between the same and a specimen preparing container inside of which a preparation solution is held and able to hold the specimen sampling part of the specimen sampler and the shaft part. This test kit enables a user to hold the cap part of the specimen sampler to sample a specimen, move the specimen to the preparation solution, then store the specimen sampling part and shaft part of the specimen sampler in the specimen preparing container, use the held cap part to seal the open part of the specimen preparing container in that state, and thereby seal the specimen preparation solution and the used specimen sampler in the specimen preparing container.

CITATION LIST

Patent Literature

PLT 1. Japanese Patent No. 4801030
PLT 2. Japanese Patent Publication No. 2013-228235A

SUMMARY OF INVENTION

Technical Problem

In each of the test kits described in PLTs 1 and 2, the specimen is prepared (extracted) in a sealed manner and a closed system is realized. However, as shown in FIG. 18, when applying the prepared extraction solution 6' to the test strip 41' or other testing means 4', it was necessary to add the extraction solution 6' dropwise from the sealed extraction container 2', so the state became a non-closed one (open one). Further closing of the system has been sought.

Further, when applying the prepared extraction solution to the test strip or other testing means, it was necessary to add for example "three drops", "five drops", etc. of the extraction solution dropwise from an addition hole provided at the surface of the housing where the test strip is held while counting the drops, so the operation was troublesome. Further, usually, the addition hole provided at the surface of the housing was a small one of several millimeters or so vertically and horizontally, so the extraction solution could not be added dropwise well and would end up splattering at different locations etc. Accurate addition of a predetermined amount was difficult.

The present invention was made in view of the above-mentioned point and has as its object the provision of a test device enabling a specimen extraction solution or other specimen sample to be added and introduced by a method other than addition dropwise to a test strip or other testing means.

Another object of the present invention is to provide a test device which enables a specimen sample in which a virus or bacteria etc. may be contained to be tested safely in a closed manner without the handler touching it and without the external environment being exposed to it and also which is simple to operate.

Solution to Problem

The test device of the present invention is provided with a testing means for testing an added extraction solution utilizing immunochromatography or nucleic acid chromatography, an extraction container in which the extraction solution is held, and a tubular guiding member having an extraction solution inflow port communicating with the extraction container in a sealed manner at one end side and having an extraction solution outflow port at the other end side. The guiding member is configured so as to have inside the tube a rod-shaped extraction solution guide having capillary action and having one end at the extraction solution outflow port side able to contact the testing means and so that the extraction solution absorbed from the extraction solution inflow port side at the extraction solution guide moves by capillary action through the inside of the extraction solution guide to be added to the testing means through the one end of the extraction solution guide contacting the testing means.

The test device of the present invention is provided with a testing means, extraction container, and guiding member. Among these, the guiding member is formed into a tubular shape. At one end side of the tube, an extraction solution inflow port is provided, while at the other end side, an extraction solution outflow port is provided. The extraction solution inflow port of this guiding member is configured to be communicated with the extraction container in a sealed manner. Due to this, the extraction solution held in the extraction container flows into the guiding member from the extraction solution inflow port. Inside the guiding member, a rod-shaped extraction solution guide is provided. The inflowing extraction solution is absorbed in this extraction solution guide having a capillary action. The extraction solution guide is arranged inside of the guiding member so that one end at the extraction solution outflow port side contacts the testing means. For this reason, the extraction solution absorbed in the extraction solution guide moves through the extraction solution guide to the extraction solution outflow port side and is added to the testing means through one end at the extraction solution outflow port side. For this reason, it is possible to simply and reliably introduce the extraction solution into the testing means without adding the extraction solution dropwise.

The testing means is provided with a housing at which an addition hole for adding extraction solution is provided and a test strip held at the inside of this housing and able to develop the extraction solution. The guiding member is configured so as to insert the extraction solution outflow port in the addition hole so as to make the above-mentioned one end of the extraction solution guide contact the test strip. When making the above-mentioned one end of the extraction solution guide contact the test strip, the outside wall near the extraction solution outflow port of the guiding member is preferably configured so as to engage with the inside wall near the addition hole of the housing.

The test device of the present invention adds the extraction solution held inside the extraction container through the extraction solution guide provided at the guiding member to the testing means. The testing means is provided with a housing in which an addition hole is provided and a test strip held in this housing. The addition hole of the housing is configured so that the extraction solution outflow port of the guiding member can be inserted into it. Due to this, one end of the extraction solution guide at the extraction solution outflow port side contacts the test strip held inside the housing through the addition hole. Due to capillary action, the extraction solution which had been absorbed at the extraction solution guide is added to the test strip. At the time of addition by this contact, the outside wall near the extraction solution outflow port of the guiding member engages with the inside wall near the addition hole of the housing, so the guiding member and the housing holding the test strip are reliably fastened. For this reason, the handler does not have to fasten them by hand. The state of contact of the one end of the extraction solution guide of the guiding member and the test strip is reliably maintained, and the extraction solution can be moved to the test strip easily and reliably. Further, the addition hole of the housing is sealed by the guiding member, so the specimen and the device etc. to which the specimen has deposited are not touched by the handler, safe testing is performed, and the used test device can be disposed of. Specifically, the test at the examination room and hospital wing in which the specimen was taken can be conducted efficiently, simply, and safely of course. The test can also be performed at schools or in the home etc. Use is also possible as an OTC test device. Further, the test can be performed in a closed manner, so it is possible to effectively prevent contamination from the outside environment in inspection using nucleic acid chromatography.

Preferably, the extraction container is provided with a barrel part, a bottom part sealing one end of the barrel part in the axial direction, and an open part provided at the other end in the axial direction of the barrel part, and the guiding member is provided with a through hole forming means for forming a through hole at the bottom part of the extraction container and is configured so that the extraction container and the extraction solution inflow port of the guiding member are communicated in a sealed manner through a through hole formed by the through hole forming means. The connection between the extraction container and the extraction solution inflow port of the guiding member is formed by breaking the bottom part of the extraction container by the through hole forming means provided at the guiding member and creating a passage. At that time, the extraction container and the extraction solution inflow port of the guiding member are connected in a sealed manner and the extraction solution flows from the extraction container to the extraction solution inflow port of the guiding member. Due to this, when desiring to add the extraction solution to the testing means, the extraction container and the guiding member can be easily connected. Further, since the extraction container and the guiding member are connected in a sealed manner, the specimen and device on which the specimen is deposited etc. are not touched by the handler, the test can be performed safely, and the used test device can be disposed of.

The through hole forming means is preferably a pointed end part formed by making the end part of the extraction solution guide at the extraction solution inflow port side pointed. In connecting the extraction container and guiding member, the bottom part of the extraction container is broken by the through hole forming means of the guiding member to form a passage. The through hole forming means is the pointed end part formed by making the end part of the extraction solution guide at the extraction solution inflow port side pointed. This pointed end part breaks through the bottom part of the extraction container to form a through hole. At that time, the extraction container and the extraction solution inflow port of the guiding member are connected in a sealed manner whereby the extraction solution flows from the extraction container to the extraction solution inflow port of the guiding member. The extraction solution guide has the function of absorbing the extraction solution and making the extraction solution move to the testing means and the function of forming a through hole in the extraction container and connecting the extraction container and the guiding member. In this way, it is possible to make this through hole forming means a simple configuration, so it is possible to simplify the structure of the guiding member.

Further, the through hole forming means is preferably a projecting tab part provided at the extraction solution inflow port. In connecting the extraction container and the guiding member, the bottom part of the extraction container is broken by the through hole forming means of the guiding member to form a passage. The through hole forming means is the projecting tab part provided at the extraction solution inflow port. This projecting tab part breaks the bottom part of the extraction container to form the through hole. At this time, the bottom part of the extraction container and the extraction solution inflow port of the guiding member are connected in a sealed manner and the extraction solution flows from the extraction container to the extraction solution inflow port of the guiding member. If inserting the extraction solution inflow port side of the guiding member into the bottom part of the extraction container, it is possible to form a through hole in the bottom part and connect the extraction container and guiding member, so it is possible to simply use the test device.

The extraction container has a barrel part, a bottom part sealing one end of the barrel part in the axial direction, and an open part provided at the other end of the barrel part in the axial direction. The open part of the extraction container is provided with at least one open part side engaging means provided at that inside wall or outside wall. The outside wall or inside wall of the guiding member near the extraction solution inflow port is preferably provided with an inflow port side engaging means for engaging with the open part side engaging means. The extraction container and the guiding member are connected in a sealed manner by engagement of the at least one open part side engaging means provided at the inside wall or outside wall of the open part of the extraction container and the inflow port side engaging means provided at the outside wall or inside wall of the guiding member near the extraction solution inflow port. Due to this, the connected state of the extraction container and the guiding member is maintained and the extraction solution can be made to easily and reliably move to the guiding member. Further, the extraction container and the guiding member are connected in a sealed manner, so the specimen and device etc. on which the specimen is deposited can be kept from being touched by the handler, the test can be performed safely, and the used test device can be safely disposed of.

The extraction container is preferably formed by a non-pliable or rigid material with a small fluid permeability. In a conventional test device, as shown in FIG. 18, the barrel part of the extraction container 2' in which the extraction solution was held was pushed in to add the extraction solution 6' dropwise, so the extraction container 2' was formed by a soft, pliable plastic. However, a soft, pliable plastic is low in density, so the water content of the extraction solution held in the extraction container passed through the walls of the extraction container as water vapor giving rise to the problem of the water content decreasing or the content ending up drying up during the storage period. However, in the present invention, there is no need to press the extraction container to add the extraction solution dropwise to the testing means. The extraction solution is added to the testing means by the capillary action of the extraction solution guide of the guiding member. For this reason, the extraction container does not have to be formed by a pliable material so that it can be pressed. Accordingly, it is possible to form the extraction container by a non-pliable or rigid material with small fluid permeability and possible to prevent the extraction solution from passing to the outside of the extraction container and the extraction solution from decreasing. Due to this, the test device need not be sealed in a package with a high gas barrier property and can be stored for a long period of time in that state.

The extraction solution guide of the guiding member is preferably a fiber bundle structure or sintered porous body. Suitable materials may be selected as the extraction solution guide for guiding the extraction solution to the testing means and making it move to the testing means.

Advantageous Effects of Invention

According to the present invention, it is possible to provide a test device having the following excellent effects:

(1) It is possible to add the extraction solution to the test strip or other testing means through the extraction solution guide of the guiding member. It is possible to simply and reliably introduce the extraction solution rather than adding the extraction solution dropwise.

(2) It is possible to add the extraction solution to the testing means in a closed manner, so the specimen and device etc. on which the specimen is deposited can be kept from being touched by the handler, the test can be performed safely, and the used test device can be safely disposed of. Further, contamination from the outside environment can be effectively prevented.

(3) It is possible to easily connect the extraction container and guiding member and conduct the test when adding the extraction solution in the extraction container to the testing means.

(4) It is not necessary to add the extraction solution dropwise to the testing means, so it is possible to form the extraction container by a non-pliable or rigid material with small fluid permeability and possible to prevent the extraction solution from passing to the outside of the extraction container and the extraction solution from decreasing. Due to this, it becomes possible to store the test device for a long period of time.

BRIEF DESCRIPTION OF DRAWINGS

FIGS. 3A and 3B are views of the test device shown in FIG. 1 wherein FIG. 3A is an enlarged axial cross-sectional view of an extraction container and FIG. 3B is a cross-sectional view along the line A-A of FIG. 3A:

FIG. 6A to FIG. 6C are explanatory views schematically showing states of use of the test device shown in FIG. 1, wherein FIG. 6A shows the state of inserting the extraction solution inflow port of the guiding member in a holding region of the bottom part of the extraction container, FIG. 6B shows the state of inserting the extraction solution outflow port of the guiding member from an addition hole of the testing means, making the projecting part comprised of the extraction solution guide abut against the test strip, and making the extraction solution guide slide upward (extraction container side), and FIG. 6C shows the state of pushing in the extraction container in the direction of the addition hole of the housing to break the sealing part of the bottom part of the extraction container by the pointed end part of the extraction solution guide of the guiding member and connect the extraction container and the guiding member:

FIG. 7A to FIG. 7C are explanatory views schematically showing other states of use of the test device shown in FIG. 1 wherein FIG. 7A shows the state of making a projecting part comprised of the extraction solution guide of the guiding member abut against the test strip while making the extraction solution guide slide upward (extraction container side) and making the extraction solution outflow port of the guiding member engage with the addition hole of the testing means, FIG. 7B shows the state of bringing the vicinity of the extraction solution inflow port of the guiding member approach and be held in the holding region of the bottom part of the extraction container, and FIG. 7C shows the state of pushing in the extraction container in the direction of the addition hole of the testing means to break the sealing part of the bottom part of the extraction container by the pointed end part of the extraction solution guide of the guiding member and connect the extraction container and the guiding member:

FIG. 8A to FIG. 8C are views showing a test device according to a second embodiment of the present invention wherein FIG. 8A is a partial enlarged axial cross-sectional view of an extraction container, FIG. 8B is an enlarged axial cross-sectional view of a guiding member, and FIG. 8C is an enlarged partial cross-sectional view of a testing means:

FIG. 9A to FIG. 9C are explanatory views schematically showing states of use of the test device according to the second embodiment of the present invention wherein FIG. 9A shows the state of holding the vicinity of the extraction solution inflow port of the guiding member in the holding region of the bottom part of the extraction container, FIG. 9B shows the state of inserting the extraction solution outflow port of the guiding member from the addition hole of the housing, making the projecting part comprised of the extraction solution guide abut against the test strip, and making the extraction solution guide slide upward (extraction container side), and FIG. 9C shows the state of pushing in the extraction container in the direction of the addition hole of the housing to break the sealing part of the bottom part of the extraction container by the projecting tab part of the guiding member and connecting the extraction container and the guiding member:

FIG. 10A to FIG. 10C are explanatory views schematically showing other states of use of the test device according to the second embodiment wherein FIG. 10A shows the state of making the projecting part comprised of the extraction solution guide of the guiding member abut against the test strip while making the extraction solution guide slide upward and making the extraction solution outflow port of the guiding member engage with the addition hole of the testing means, FIG. 10B shows the state of trying to make the vicinity of the extraction solution inflow port of the guiding member approach and be held at the holding region of the bottom part of the extraction container, and FIG. 10C shows the state of pushing in the extraction container in the direction of the addition hole of the testing means to break the sealing part of the bottom part of the extraction container by the projecting tab part of the guiding member and connecting the extraction container and guiding member:

FIG. 11A to FIG. 11C are views showing a test device according to a third embodiment of the present invention wherein FIG. 11A is an enlarged axial cross-sectional view of an extraction container, FIG. 11B is an enlarged axial cross-sectional view of a guiding member, and FIG. 11C is an enlarged partial cross-sectional view of a testing means:

FIG. 12A to FIG. 12C are explanatory views schematically showing the states of use of the test device according to the third embodiment of the present invention wherein FIG. 12A shows the state of trying to fit the guiding member in the open part of the extraction container, FIG. 12B shows the state of fitting the extraction solution inflow port of the guiding member in the open part of the extraction container and connecting the extraction container and the guiding member, and FIG. 12C shows the state of inserting the extraction solution outflow port of the guiding member into the addition hole of the housing, making the projecting part comprised of the extraction solution guide abut against the test strip, and making the extraction solution guide slide upward (extraction container side):

FIG. 13A to FIG. 13E are views of a guiding member of a test device according to a fourth embodiment of the present invention wherein FIG. 13A is a plane view, FIG. 13B is a cross-sectional view along the line B1-B1 of FIG. 13A, FIG. 13C is a cross-sectional view along the line B2-B2 of FIG. 13A, FIG. 13D is an explanatory view showing the case of omission of the extraction solution guide from FIG. 13B, and FIG. 13E is a cross-sectional view at the position of the line B3-B3 of FIG. 13B.

FIG. 15A to FIG. 15F are views showing a guiding member of a test device according to a fifth embodiment of the present invention where FIG. 15A is a plane view, FIG. 15B is a cross-sectional view along the line C1-C1 of FIG. 15A, FIG. 15C is a cross-sectional view along the line C2-C2 of FIG. 15A, FIG. 15D is a cross-sectional view showing the case of omitting the extraction solution guide from FIG. 15B, FIG. 15E is a cross-sectional view at the position of the line C3-C3 of FIG. 15B, and FIG. 15F is a cross-sectional view at the position of the line C4-C4 of FIG. 15B:

DESCRIPTION OF EMBODIMENTS

Hereinafter, referring to FIG. 1 to FIG. 7, a first embodiment of the present invention will be explained.

Figure 1:
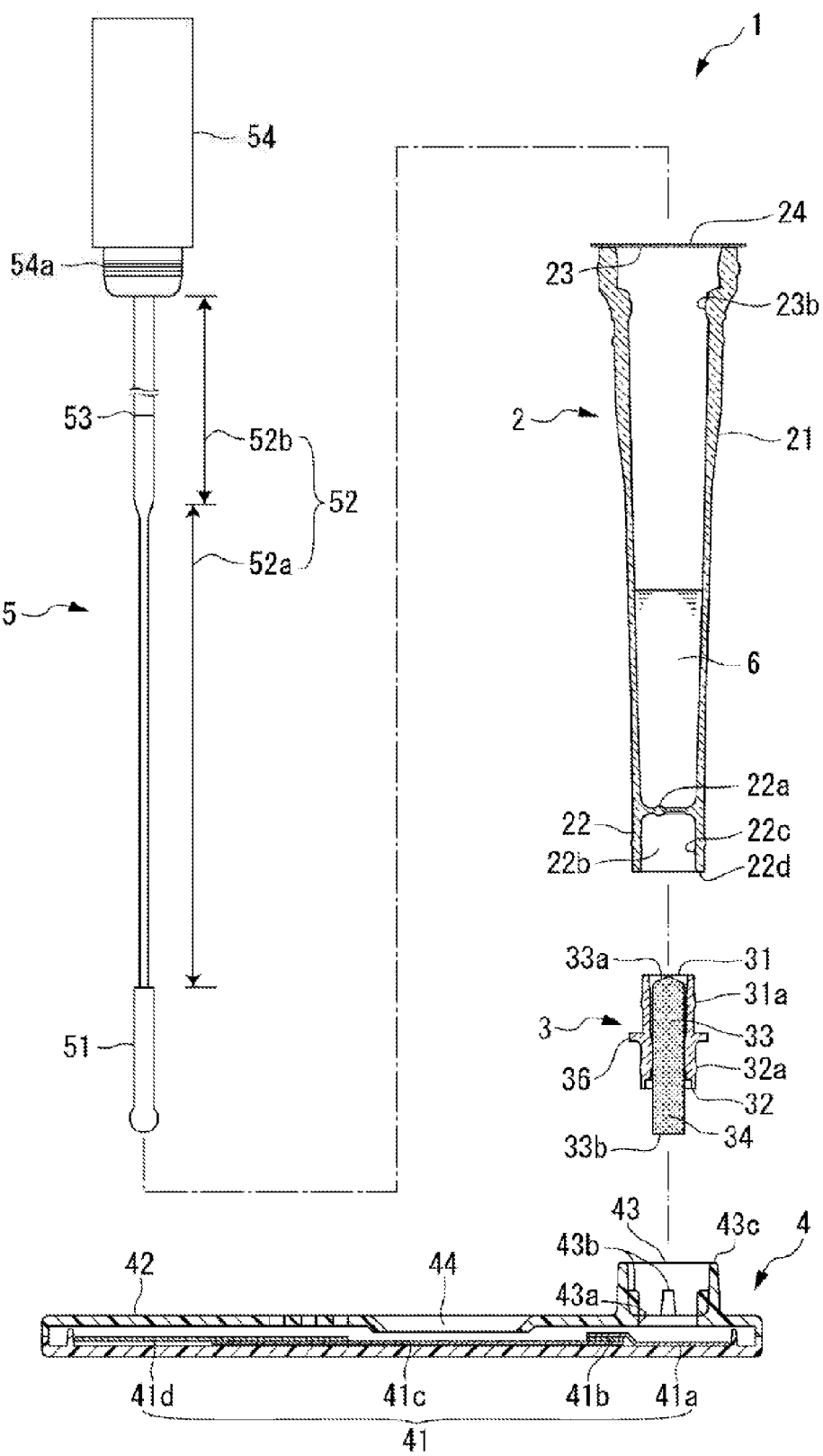
FIG. 1 gives a cross-sectional view of an extraction container, guiding member, and testing means of a test device according to a first embodiment of the present invention and a front view of a specimen sampler.
Figure 2:
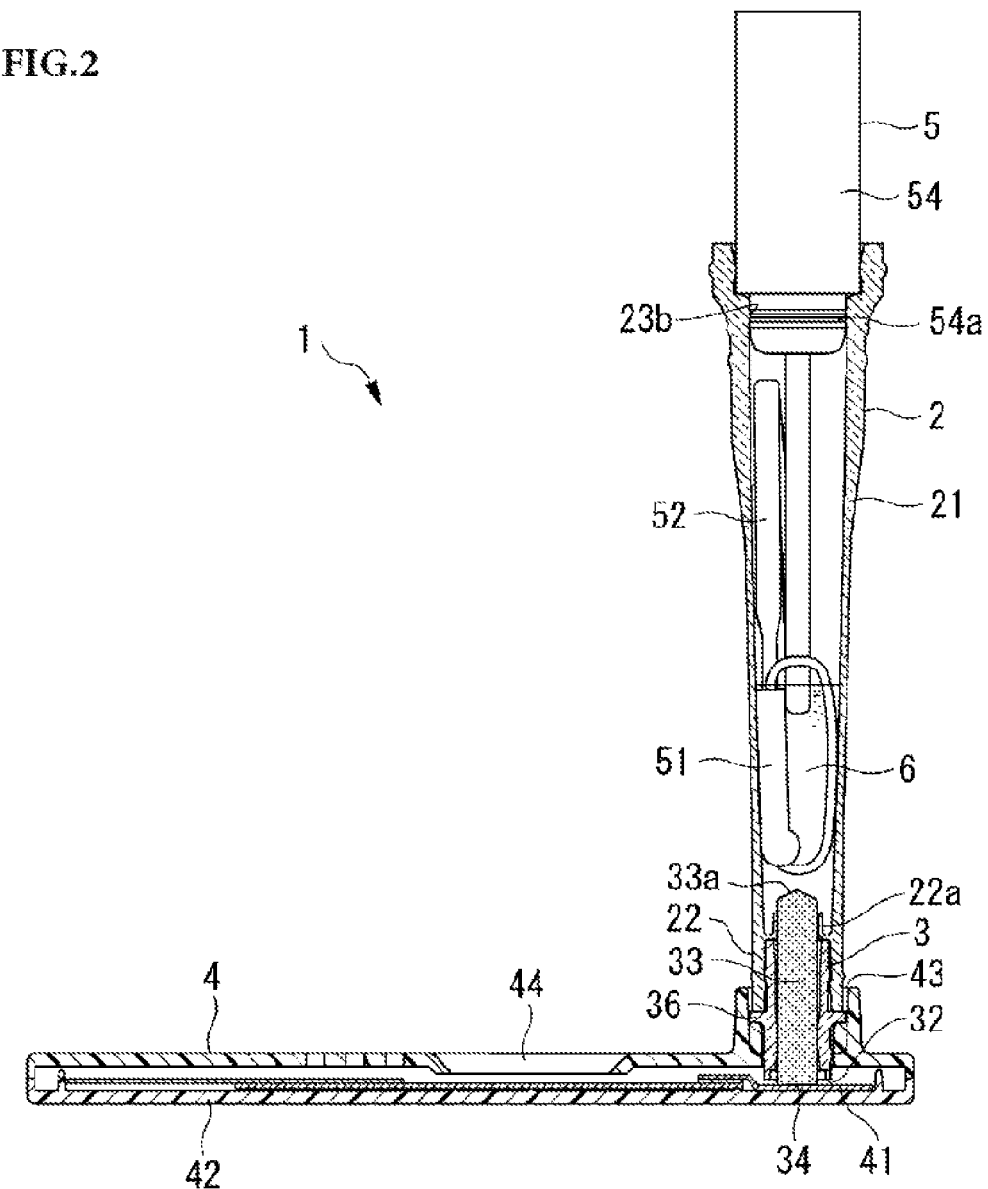
FIG. 2 is an explanatory view showing the state when using the test device of FIG. 1 to add an extraction solution to the testing means.

As shown in FIG. 1, the test device 1 according to the first embodiment of the present invention is provided with an extraction container 2, a guiding member 3, a testing means 4, and a specimen sampler 5. The test device 1 according to the present embodiment shows a lateral flow type test device utilizing immunochromatography used for testing the influenza virus as one example, but the test device of the present invention also includes a test device utilizing nucleic acid chromatography. As the test coverage, as examples, the influenza virus, RS virus, Group A β hemolytic streptococcus, adenovirus, norovirus, rotavirus, sapovirus, mycoplasma pneumonia, and other microorganisms, microorganism-, plant-, and nonhuman animal-derived proteins, microorganism-, plant-, and nonhuman animal-derived nucleic acid, hemoglobin, transferrin, and other human-derived proteins, human-derived nucleic acids, tumor markers, hormones, vitamins, bioactive amines, prostaglandins, antibiotics, allergens, agrochemicals, etc. may be mentioned. By testing using this test device 1, as shown in FIG. 2, rather than adding the extraction solution dropwise, it is possible to simply and reliably add and introduce the extraction solution 6 in a closed manner to the testing means 4.

Figure 3A:
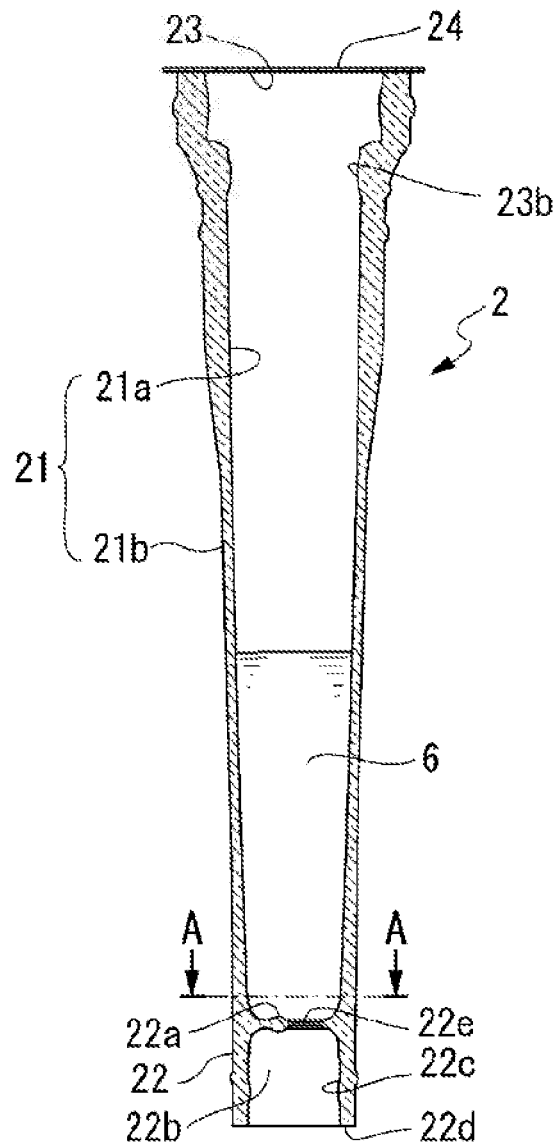

First, based on FIG. 1 to FIG. 3, the extraction container 2 will be explained. The extraction container 2 in the present embodiment is a tubular container inside of which is held an extraction solution 6 for dispersing or dissolving a specimen. It has a barrel part 21, a bottom part 22 sealing one end side of the barrel part 21 in the axial direction, and an open part 23 opening at the other end side. This open part 23 is provided in advance with a lid member 24 for preventing leakage of the held extraction solution 6 to the outside or contamination by foreign matter. This lid member 24 is configured to be able to be detached for inserting the specimen sampler 5 and can open the open part 23 of the extraction container 2. Specifically, as the lid member 24, a film seal lid covering the open part 23 by attaching a plastic film to the end face of the open part 23 by a binder or heat seal, ultrasonic welding, etc., screw type lid, push-in type cap, etc. can be used. By detaching this lid member 24, the sealed state of the extraction container 2 is broken once and the specimen sampling part 51 and shaft part 52 of the specimen sampler 5 after sampling the specimen can be inserted into the container. Further, at the inside wall 21a of the extraction container 2 near the open part 23, a projecting type open part side sealing part 23b is provided engaging with the cap sealing part 54a of the specimen sampler 5 explained later to seal the open part 23. Note that, in tests utilizing nucleic acid chromatography, the specimen sampler 5 is not used. As a specimen, a PCR product or other nucleic acid solution is added to the extraction solution 6, then a cap etc. is used to seal the open part 23.

Figure 3B:
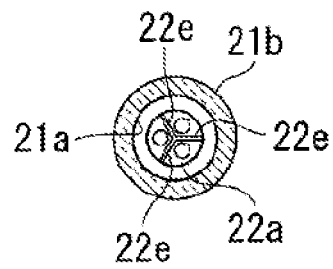

On the other hand, at the bottom part 22 of the extraction container 2, a sealing part 22a is provided at the position of the open part 23 side separated by a predetermined distance from the end part 22d at the bottom part side. As shown in FIG. 3B, this sealing part 22a is provided with stripe-shaped breaking parts 22e formed thinly just at that part to enable the through hole forming means comprised of the pointed end part 33a provided at the later explained guiding member 3 to easily form a through hole. In the present embodiment, the breaking parts 22e are formed by three straight stripe parts connected at the center of a circle, but the invention is not limited to this. Between the sealing part 22a and end part 22d of the bottom part 22, there is a holding region 22b for holding the extraction solution inflow port 31 side of the guiding member 3. At the inside wall 21a of the holding region 22b, a bottom part side engaging part 22c engaging with an inflow port side engaging part 31a provided at the outside wall of the extraction solution inflow port 31 of the guiding member 3 is provided. In the present embodiment, as the bottom part side engaging part 22c, a recessed part running continuously along the peripheral direction at the inside wall of the bottom part 22 is provided. This bottom part side engaging part 22c may be any structure able to engage with the inflow port side engaging part 31a of the guiding member 3. Specifically, for example, one or more projecting parts, recessed parts, projecting grooves, recessed grooves, or ribs, one or more projecting parts, recessed parts, projecting grooves, recessed grooves, or ribs running continuously in ring shapes in the peripheral direction, and one or more projecting parts, recessed parts, projecting grooves, recessed grooves, or ribs running continuously in spiral shapes in the peripheral direction, or any combination of the same at the inside wall 21a or outside wall 21b of the bottom part 22 may be mentioned.

The extraction container 2 is preferably formed by a non-pliable or rigid material with a small fluid permeability. Specifically, while not particularly limited, an olefinic thermoplastic elastomer, polypropylene resin, high density polyethylene resin, glass, etc. may be suitably used. A polypropylene resin or non-cross-linkable olefinic thermoplastic elastomer is particularly preferable. Note that, when using glass to form the extraction container 2, in an embodiment like in the present embodiment where a through hole is formed in the sealing part 22a of the bottom part 22 at the time of use, it is preferable to form only the sealing part 22a by aluminum or another metal film or plastic etc. so as to enable a through hole to be formed in the sealing part 22a. The extraction container 2 in the present embodiment is formed integrally using a non-cross-linkable type olefinic thermoplastic elastomer as a non-pliable material. In the test device of the present invention, there is no need to press the extraction container 2 to add the extraction solution 6 dropwise to the testing means 4. The extraction solution 6 is added to the test strip 41 of the testing means 4 by capillary action of the extraction solution guide 33 of the guiding member 3 explained later. For this reason, there is no need to form the extraction container 2 by a pliable material which can be pressed. The extraction container 2 can be formed by a non-pliable or rigid material with small fluid permeability, and the extraction solution 6 can be prevented from passing to the outside of the extraction container 2 and the extraction solution 6 can be prevented from decreasing. Due to this, it becomes possible to store the test device 1 over a long period of time in its original state without sealing it in a package with a high gas barrier property. Note that, the extraction container 2 may also be formed by a plastic material with pliability. In this case, in the same way as the conventional method of use, it is possible to press against the barrel part of the extraction container 2 to add the solution dropwise from the extraction solution outflow port 32 of the guiding member 3 to apply it to the testing means 4.

Figure 4:
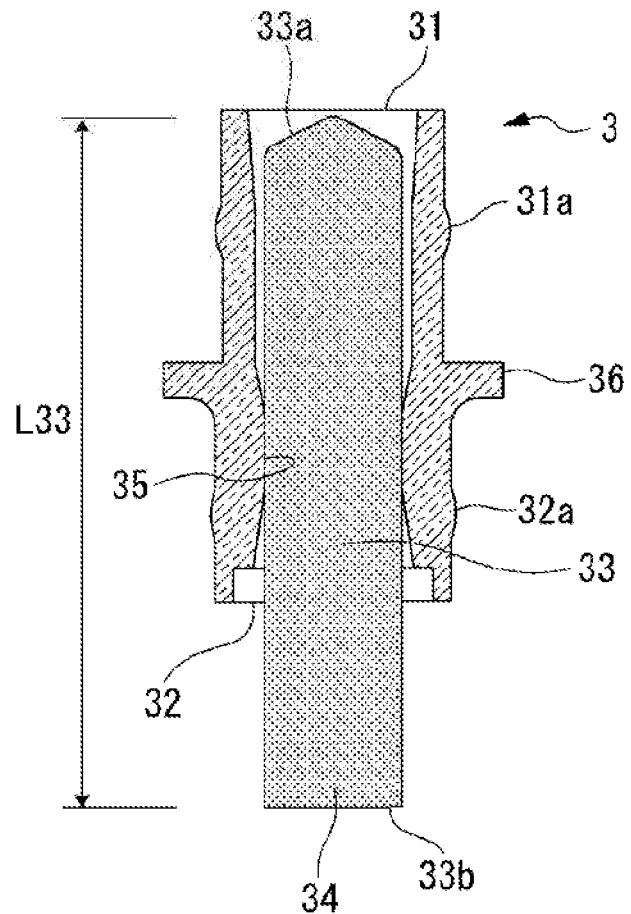
FIG. 4 is an enlarged axial cross-sectional view of the guiding member in the test device shown in FIG. 1.

Next, based on FIG. 4, the guiding member 3 will be explained. The guiding member 3 in the present embodiment is formed into a tubular shape which has an extraction solution inflow port 31 at one end side, has an extraction solution outflow port 32 at the other end side, and holds the extraction solution guide 33 inside it. The extraction solution inflow port 31 is formed so as to be fit in a sealed manner into the holding region 22b provided between the end part 22d and sealing part 22a of the bottom part 22 of the extraction container 2. At the outside wall of the extraction solution inflow port 31, an inflow port side engaging part 31a engaging with the bottom part side engaging part 22c of the extraction container 2 is provided. In the present embodiment, as shown in FIG. 4, as the inflow port side engaging part 31a, a projecting part continuous running along the peripheral direction at the outside wall near the extraction solution inflow port 31 is provided. This inflow port side engaging part 31a engages with the bottom part side engaging part 22c of the extraction container 2 as explained above to reliably fasten the two and connect them in a sealed manner. This inflow port side engaging part 31a may be any structure so long as a structure able to engage with the of the bottom part side engaging part 22c of the extraction container 2. Specifically, for example, one or more projecting parts, recessed parts, projecting grooves, recessed grooves, or ribs, one or more projecting parts, recessed parts, projecting grooves, recessed grooves, or ribs running continuously in ring shapes in the peripheral direction, and one or more projecting parts, recessed parts, projecting grooves, recessed grooves, or ribs running continuously in spiral shapes in the peripheral direction, or any combination of the same at the inside wall or outside wall of the extraction solution inflow port 31 may be mentioned.

On the other hand, the extraction solution outflow port 32 is formed to as to be able to be inserted into the addition hole 43 of the housing 42 of the testing means 4. At the outside wall near the extraction solution outflow port 32, an outflow port side engaging part 32a engaging with the addition hole side engaging part 43a of the addition hole 43 of the testing means 4 is provided. In the present embodiment, in the same way as the inflow port side engaging part 31a, as the outflow port side engaging part 32a, a projecting part continuously running along the peripheral direction at the outside wall near the extraction solution outflow port 32 is provided. This outflow port side engaging part 32a engages with the addition hole side engaging part 43a of the addition hole 43 of the testing means 4 to reliably fasten the two and connect them in a sealed manner. This outflow port side engaging part 32a may be any structure so long as a structure able to engage with the addition hole side engaging part 43a of the testing means 4. For example, one or more projecting parts, recessed parts, projecting grooves, recessed grooves, or ribs running continuously in ring shapes in the peripheral direction, one or more projecting parts, recessed parts, projecting grooves, recessed grooves, or ribs running continuously in spiral shapes in the peripheral direction, or any combination of the same at the outside wall or inside wall near the extraction solution outflow port 32 may be mentioned.

Further, at the outside wall of the tubular member of the guiding member 3, a flange part 36 is provided sticking out outward along the peripheral direction at part of about half of the length of the tubular member. This flange part 36 is supported at the guiding member support part 43b provided at the addition hole 43 of the testing means 4 explained later and functions so as to maintain the state of abutment when the end of the extraction solution guide 33 sticking out, that is, the projecting part 34, abuts against the testing means 4. For this reason, the capillary action of the extraction solution guide 33 stably functions and the extraction solution is efficiently added to the test strip 41. Furthermore, when the extraction solution inflow port 31 of the guiding member 3 is fit in the holding region 33b of the bottom part 22 of the extraction container 2, the end part 33d of the extraction container 2 abuts against the top side of this flange part 36 (extraction container 2 direction) and is sealed, so the extraction container 2 and the guiding member 3 are connected in a sealed manner and leakage of the extraction solution 6 to the outside environment can be prevented. In the same way, when the extraction solution outflow port 32 of the guiding member 3 is fit in the addition hole 43 of the housing 42 of the testing means 4, the guiding member support part 43b abuts against the bottom side of this flange part 36 (testing means 4 direction) and is sealed, so the guiding member 3 and testing means 4 are connected in a sealed manner and leakage of the extraction solution 6 to the outside environment can be prevented.

In the space at the inside of the tube connecting the extraction solution inflow port 31 and extraction solution outflow port 32 of the guiding member 3, a rod-shaped extraction solution guide 33 is held. In the present embodiment, the extraction solution guide 33 is formed as a substantially circular columnar shape, but it may also be formed into various other shapes such as an oval columnar shape and polygonal columnar shape. Further, the shape in the axial cross-section need not be constant. The outflow port side end part 33b of the extraction solution guide 33 held in the guiding member 3 forms a projecting part 34 arranged so as to stick out from the extraction solution outflow port 32. Note that, if the outflow port side end part 33b of the extraction solution guide 33 can abut against the test strip 41 of the testing means 4 explained later, it need not stick out from the extraction solution outflow port 32. The extraction solution guide 33 is arranged to be anchored by the guide holding part 35 provided inside the tube and so as not to detach from the inside of the tube of the guiding member 3, but is anchored to be able to slide inside the tube when force is applied from the extraction solution outflow port 32 side to the extraction solution inflow port 31 side. In the present embodiment, the guide holding part 35 is formed into a projecting shape continuously running along the peripheral direction at the inside wall of the tube of the guiding member 3. The part of the guide holding part 35 is made slightly narrower in inside diameter of the tube. In this way, the guide holding part 35 is configured so that the extraction solution guide 33 is anchored inside the tube of the guiding member 3 to an extent by which the extraction solution guide 33 can slide through the inside of the tube when a constant force is applied to the outflow port side end part 33b.

Regarding the shape of the end part of the extraction solution guide 33, the outflow port side end part 33b is configured in a substantially flat shape with a large contact area so as to increase the efficiency of movement of the extraction solution 6 since the extraction solution 6 moves to the testing means 4 through this outflow port side end part 33b. However, it may be any shape so long as enabling movement of the extraction solution 6 to the testing means 4. On the other hand, at the end part of the extraction solution guide 33 at the extraction solution inflow port 31 side, in the present embodiment, a pointed end part 33a with a pointed front end is provided so as to be able to break through the sealing part 22a of the extraction container 2 and form a through hole. The pointed end part 33a is not particularly limited in shape, but it can be formed in a cone or tapered shape. The pointed end part 33a of this extraction solution guide 33, as shown in the explanatory views of FIG. 6 and FIG. 7, sticks out from the extraction solution inflow port 31 of the guiding member 3 and breaks through the sealing part 22a to connect the extraction container 2 and guiding member 3 when fitting the guiding member 3 into the holding region 22b of the bottom part 22 of the extraction container 2.

The length L33 of the extraction solution guide 33 should be a length of an extent whereby the outflow port side end part 33b of the extraction solution guide 33 can abut against the test strip 41 of the testing means 4 at the time of use while the pointed end part 33a can contact and break through the sealing part 22a of the bottom part 22 of the extraction container 2. It is preferably formed longer than the tube length of the guiding member 3. In the present embodiment, the tube length of the guiding member 3 is 14 mm, while the length L33 of the extraction solution guide 33 is formed as 22 mm. Further, the extraction solution guide 33 is formed to a diameter of 3.5 mm.

The extraction solution guide 33 may be any one which has a capillary action, for example, a fiber bundle structure, sintered porous body, paper, sponge, nonwoven fabric, woven fabric, etc. In the present invention, from the viewpoint of excellent capillary action, a fiber bundle structure or sintered porous body is suitably used. A "fiber bundle structure" is a structure formed by bundling and bonding synthetic resin fibers, pulp fibers, glass fibers, or other fibers and filaments by heat or other resins etc. and has a capillary action making a liquid move from one end to the other end side of the fibers forming the fiber bundle. As the synthetic resin fibers, fibers comprised of a polyamide, acryl, rayon, acetate, polyester, polyvinylchloride, polyethylene, polypropylene, etc. may be suitably selected. As the extraction solution guide 33 in the present embodiment, a fiber bundle structure formed by a fiber bundle mainly comprised of polyester fibers bonded by a polyurethane resin is selected. The fiber thickness of the fiber bundle structure, from the viewpoint of that capillary action, is preferably 1 to 10 denier, more preferably 1 to 7 denier, particularly preferably 2 to 5 denier. Further, from the viewpoint of the capillary action or the later explained absorption ability and filtration performance, the porosity of the fiber bundle structure is preferably 35 to 80%, more preferably 40 to 70%, particularly preferably 45 to 65%. On the other hand, the "sintered porous body" is a porous body fouled by a resin or metal or other particles, ceramic powder, or metal fibers sintered in a state entangled three-dimensionally and has a capillary action making a liquid move through the three-dimensional mesh structure. As the material of the particles, a resin is preferable. Polyethylene (low density polyethylene, high density polyethylene, and ultrahigh molecular weight polyethylene), polypropylene, polystyrene, polymethyl methacrylate, etc. may be suitably selected. The pore size of the sintered porous body, from the viewpoint of the capillary action, is preferably 10 to 200 µm, more preferably 20 to 100 µm. Note that, the fiber bundle structure, sintered porous body, or other extraction solution guide 33 may raise the hydrophilicity and absorption ability by treatment by a surfactant etc. The above-mentioned fiber bundle structure, sintered porous body, and other extraction solution guides 33 have capillary action and have high absorption ability. For this reason, it is possible to quickly absorb the extraction solution 6 flowing in from the extraction container 2 and quickly guide it to the testing means 4 by capillary action. Furthermore, the fiber bundle structure or other extraction solution guide 33 is high in liquid holding ability, so after connecting the extraction container 2 and the guiding member 3, it is possible to safely conduct the test without the extraction solution 6 immediately ending up dripping from the outflow port side end part 33b of the extraction solution guide 33. Further, after the amount of extraction solution 6 which the test strip 41 of the testing means 4 can absorb is added through the extraction solution guide 33, no further extraction solution 6 is added from the extraction solution guide 33 to the test strip 41, so it is possible to safely conduct the test without the extraction solution 6 leaking from the testing means 4. Furthermore, the fiber bundle structure, sintered porous body, or other extraction solution guide 33 structurally has a filtration performance as well. It also has the action of removing unnecessary substances contained in the extraction solution 6 such as highly viscous secretions or pieces of cells derived from the sampled specimens. For this reason, there is no need to filter the extraction solution by a separately prepared filter device etc., so the configuration of the test device can be made simple.

Further, the guiding member 3 is preferably formed by a transparent or translucent plastic so as to enable visual confirmation as to whether the pointed end part 33a of the extraction solution guide 33 held inside the tube has broken through the sealing part 22a of the extraction container 2 and the extraction container 2 and the guiding member 3 has been connected. While not particularly limited, specifically a polyethylene, polypropylene, nylon, polyester, polystyrene, or other synthetic resin can be suitably used.

Next, based on FIG. 1 and FIG. 5, the testing means 4 will be explained. In the present embodiment, the testing means 4 is basically configured by a test strip 41 developed by an extraction solution 6 and displaying the test results and a housing 42 holding the test strip 41. On the surface of the housing 42, an approximately circular shaped addition hole 43 for adding the extraction solution 6 is provided. Furthermore, a judging window 44 for displaying the test results is provided. The addition hole 43 has a tubular addition hole wall 43c formed in the peripheral direction of the hole while sticking out substantially vertically upward. It is formed to be able to support and fasten the guiding member 3 and to prevent leakage of the added extraction solution 6. At the inside wall of the addition hole wall 43c, an addition hole side engaging part 43a is provided for inserting the extraction solution outflow port 31 of the guiding member 3 into the addition hole 43 and for stably maintaining the abutting state when making the outflow port side end part 33b abut against the test strip 41. Specifically, the inside wall of the addition hole wall 43c is provided with a projecting addition hole side engaging part 43a continuously running in the peripheral direction. This addition hole side engaging part 43a engages with the outflow port side engaging part 32a of the guiding member 3 and reliably fastens and connects the two and can seal the space between the guiding member 3 to which the extraction solution 6 is added and the testing means 4 and prevent leakage of the extraction solution 6. This addition hole side engaging part 43a may be any structure so long as a structure able to engage with the outflow port side engaging part 32a of the guiding member 3. For example, one or more projecting parts, recessed parts, projecting grooves, recessed grooves, or ribs running continuously in ring shapes in the peripheral direction, one or more projecting parts, recessed parts, projecting grooves, recessed grooves, or ribs running continuously in spiral shapes in the peripheral direction, or any combination of the same at the inside wall or outside wall of the addition hole 43 may be mentioned.

Furthermore, at the inside wall of the top side of the above-mentioned addition hole side engaging part 43a (direction of end part of addition hole wall 43c), four projecting guiding member support parts 43b are provided at substantially equal intervals in the peripheral direction. The step parts of these guiding member support parts 43b support and fasten the above-mentioned flange part 36 of the guiding member 3 to determine the position in the vertical direction when the guiding member 3 abuts against the test strip 41 of the testing means 4. For this reason, when the projecting part 34 comprised of the extraction solution guide 33 of the guiding member 3 abuts against the test strip 41, that abutting state is held and it is possible to prevent the extraction solution guide 33 from ending up being held inside the extraction solution outflow port 32 and no longer abutting against the strip. In the present embodiment, the guiding member support parts 43b are comprised of projecting step parts continuously extending in the upward direction from the addition hole side engaging part 43a, but the addition hole side engaging part 43 and the guiding member support parts 43b may be separately fainted. As one example, it is possible to use the top end part of the addition hole wall 43c as a guiding member support part 43b. In that case, the guiding member 3 can be supported and fastened by placing the flange part 36 of the guiding member 3 on the top end part of the addition hole wall 43c and supporting and fastening it. Further, by the flange part 36 of the guiding member 3 abutting against the guiding member support part 43b of the addition hole 43, the guiding member 3 and the testing means 4 are further sealed and leakage of the extraction solution 6 can be prevented.

Figure 5:
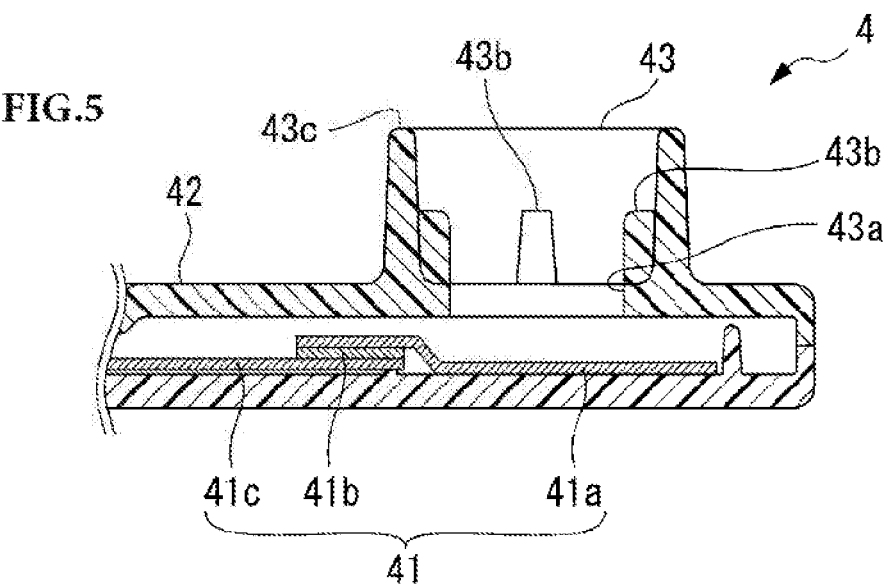
FIG. 5 is an enlarged partial cross-sectional view of the testing means in the test device shown in FIG. 1.

Further, as shown in FIG. 1 and FIG. 5, the test strip 41 in the present embodiment is configured as a lateral flow type test strip utilizing immunochromatography and has a sample pad 41a absorbing the added extraction solution 6, a conjugate pad 41b containing a labeled antibody etc., a membrane 41c containing a supplementary antibody etc. and displaying the test results, and absorption pad 41d absorbing the excess extraction solution. Further, when making the testing means 4 a testing means 4 utilizing nucleic acid chromatography, the test strip 41 should be one for nucleic acid chromatography. A test strip 41 utilizing nucleic acid chromatography is as one example comprised of a sample pad 41a absorbing the added extraction solution 6, a conjugate pad 41b containing latex particles or other labeling substances, a membrane 41c containing a supplementary probe etc. and displaying the test results, and an absorption pad 41d absorbing the excess extraction solution. The extraction solution 6 introduced from the addition hole 43 through the guiding member 3 is first introduced to the sample pad 41a by capillary action, then moves by capillary action to the conjugate pad 41b, membrane 41c, and absorption pad. The test results displayed on the membrane 41c can be confirmed through the judging window 44. The test strip 41 is not limited to one of the above configuration. A flow through type test strip or other configuration suitably combined are also broadly included.

The test strip 41 can also be designed to absorb only a certain amount of extraction solution 6 by adjusting the specifications of the materials forming the test strip 41 etc. The extraction solution guide 33 does not add any further extraction solution 6 to a test strip 41 which has absorbed a certain amount of extraction solution 6 by that capillary action, so a constant amount of extraction solution 6 may always be added to the test strip 41 through the extraction solution guide 33.

Note that, to avoid contact with the extraction solution 6 added to the testing means 4 and further make the test device 1 closed, it is possible to make the judging window 44 part of the housing 42 by a transparent plastic film or shrink wrap the parts other than the addition hole 43 of the housing with a transparent plastic film. Further, it is also possible to laminate at least the part of the test strip 41 exposed from the judging window 44 with a plastic film.

Next, based on FIG. 1, a specimen sampler 5 for sampling the specimen to be tested will be explained. As shown in FIG. 1, the specimen sampler 5 in the present embodiment is mainly comprised of a shaft part 52, a specimen sampling part 51 provided integrally at one end of the shaft part 52 in the longitudinal direction, and a cap part 54 provided integrally at the other end in the longitudinal direction. It is configured to be able to be inserted from the nostril or mouth etc. of the patient and to swipe deep into the nose or throat by the specimen sampling part 51 provided at the front end part of the same to sample a specimen. In this, the cap part 54 is provided with a cap sealing part 54a able to engage with the open part side sealing part 23b provided at the inside wall near the open part 23 of the extraction container 2 and seal the open part 23. Due to this, as shown in FIG. 2, it is possible to bend and place inside the extraction container 2 the specimen sampling part 51 and shaft part 52 of the specimen sampler 5 after sampling a specimen and seal the open part 23 by the cap part 54 in that state to seal the extraction container 2. Note that, the specimen sampler 5 can also be configured without the cap part 54, i.e., by only the specimen sampling part 51 and the shaft part 52. Further, depending on the inspected object, the shaft part 52 may also be formed shorter in length of the shaft part 52.

As shown in FIG. 1, in the present embodiment, the shaft part 52 of the specimen sampler 5 is configured by a pliable part 52a and a base part 52b. The pliable part 52a is a small diameter part from a predetermined position to the specimen sampling part 51 and has pliability enabling it to deform by application of stress. The base part 52b is the part of a thick diameter from the boundary with the pliable part 52a to the cap part 54 and has a rigidity higher than the pliable part 52a. For this reason, as shown in FIG. 2, when holding the specimen sampling part 51 and shaft part 52 of the specimen sampler 5 in the extraction container 2, by applying force to the pliable part 52a of the shaft part 52, the pliable part 52a can be bent or curved to deform it and shorten the length of the shaft part 52 in that state. At a predetermined position of the base part 52b of the shaft part 52, a notch 53 is provided for easily cutting and dividing the base part 52b in a direction vertical to the axial direction. By bending the base part 52 at the position where the notch 53 is provided, the base part 52b is easily cut and divided in the axial direction, so the length of the shaft part 52 in the state held in the extraction container 2 can be further shortened.

The material forming the shaft part 52 is not particularly limited, but polystyrene, polyethylene, polypropylene, nylon, polyester, or other resin or paper etc. may be suitably used. Further, in the present embodiment providing a pliable part 52a at the shaft part 52, a material which has pliability for deforming due to application of stress is selected. Further, the specimen sampling part 51 need only be one which can pick up a specimen. A cotton ball, a cotton swab provided with a cotton ball, a sponge, brush, etc. may be suitably selected. In particular, since the specimen sampling ability is excellent, a cotton swab processing synthetic fiber by flocking to form a cotton ball may be suitably used. The specimen sampled by such a specimen sampler 5 is not particularly limited, but nasal cavity or throat swabs, nasal discharge, sputum, urine, blood, plasma, serum, feces, rectal swabs, mucous membrane swabs, saliva, tears, amniotic fluid, biotissue swabs, spinal fluid, and pus of humans and nonhuman animals plus food swabs, food extraction solutions, beverages, tap water, wastewater, environmental water, soil, and plant extracts etc. may be mentioned. Note that, the specimen sampler 5 is not used for tests using nucleic acid chromatography.

Next, based on FIG. 1, FIG. 2, and FIG. 6, the method of use of the test device 1 according to the present embodiment will be explained. Note that, in FIG. 6, the specimen sampler 5 is omitted.

First, the specimen sampler 5 shown in FIG. 1 is used to sample a specimen (not shown). When sampling a specimen, the handler can grip the cap part 54 and operate the specimen sampling part 51 and shaft part 52. The specimen is sampled from the patient's nostrils, throat, mucous membrane, urinary tract, ovary, vagina, feces, urine, sputum etc. by swabbing by the specimen sampling part 51. The sampled specimen is held deposited on the specimen sampling part 51.

Next, the specimen sampler 5 after sampling of the specimen is inserted from the open part 23 of the extraction container 2 in the state holding the cap part 54 with the specimen sampling part 51 at the front to store the specimen sampling part 51 and the shaft part 52 inside of the container from the open part 23 of the extraction container 2. At this time, as shown in FIG. 2, the pliable part 52a of the shaft part 52 was bent to deform it to a loop shape and the position of the shaft part 52 with the notch 53 was pushed against the end edge of the open part 23 to bend it whereby the shaft part 52 was broken and split at that position. Due to this, it is possible to substantially shorten the length of the shaft part 52 etc. of the specimen sampler 5 and store the part inside the extraction container 2. After storing it there, the cap sealing part 54a of the cap part 54 is used to seal the open part 23 of the extraction container 2.

Next, as shown in FIG. 6A, the extraction solution inflow port 31 side of the guiding member 3 is pushed into the holding region 22b of the bottom part 22 of the extraction container 2 to attach it there. At this stage, the extraction container 2 and the guiding member 3 are not connected and the two are provisionally fitted.

Next, as shown in FIG. 6A and FIG. 6B, the projecting part 34 of the guiding member 3 provisionally fit in the extraction container 2 is inserted into the addition hole 43 of the housing 42 of the testing means 4. If holding the barrel part 21 etc. of the extraction container 2 and inserting the guiding member 3 in the addition hole 43, the projecting part 34 of the guiding member 3 abuts against the sample pad 41a of the test strip 41 of the testing means 4. Furthermore, if applying force in the direction from the extraction container 2 side to the testing means 4 side, as shown in FIG. 6B, the operations (i) to (iii) occur: (i) the extraction solution guide 33 comprised of the fiber bundle structure slides through the inside of the tube of the guiding member 3 to the extraction solution inflow port 31 side (top side), (ii) the outflow port side engaging part 32a of the guiding member 3 and the addition hole side engaging part 43a of the testing means 4 engage and the guiding member 3 and the testing means 4 are connected in a closed manner, and (iii) the flange part 36 of the guiding member 3 abuts against the guiding member support part 43b of the testing means 4 whereby the position in the vertical direction is determined.

Next, as shown in FIG. 6C, furthermore, if applying force in the direction from the barrel part 21 side to the testing means 4 side of the extraction container 2, the pointed end part 33a of the extraction solution guide 3 sliding to the extraction solution inflow port 31 side (top side) reaches the sealing part 22a of the extraction container 2 and this pointed end part 33a breaks the breaking part 22e of the sealing part 22a to form the through hole 25. The fiber bundle structure forming the extraction solution guide 33 is further provided with a certain hardness of an extent enabling the sealing part 22a to be broke through and can easily form the through hole 25. Due to this, the extraction container 2 and the guiding member 3 are connected and the extraction solution 6 which had been held in the extraction container 2 passes through the through hole 25 or the extraction solution guide 33 sticking out from the through hole 25 to the extraction solution inflow port 31 of the guiding member 3. Further, the end part 22d of the extraction container 2 abuts against the flange part 36 of the guiding member 3 and the bottom part side engaging part 22c of the extraction container 2 and the inflow port side engaging part 31a of the guiding member 3 are engaged. Due to this, the extraction container 2 and the guiding member 3 are connected in a sealed manner, so it is possible to prevent leakage of the extraction solution 6 flowing into the guiding member 3 to the outside environment. The extraction solution 6 flowing into the extraction solution inflow port 31 of the guiding member 3 and the extraction solution 6 absorbed through the sticking out pointed end part 33a are sucked into the extraction solution guide 33 and moved by capillary action to the outflow port side end part 33b of the extraction solution guide 33. The outflow port side end part 33b of the extraction solution guide 33 abuts against the sample pad 41a of the test strip 41 of the testing means 4, so the extraction solution 6 moves through the outflow port side end part 33b of this guiding member 3 to the sample pad 41a. In this way, rather than adding the extraction solution 6 dropwise, it is possible to simply and reliably introduce the extraction solution 6 to the test strip 41 in a closed manner. The present embodiment is configured so that the extraction solution 6 flowing into the extraction solution inflow port 31 is absorbed in the extraction solution guide 33 and moves to the test strip 41 of the testing means 4 through the outflow port side end part 33b of the extraction solution guide 33. The extraction solution 6 is added to the test strip 41 utilizing the capillary action of the extraction solution guide 33 comprised of the fiber bundle structure, so the extraction solution 6 which the extraction solution guide 33 absorbs and holds inside it is added to the test strip 41 in accordance with the state of development of the extraction solution 6 in the test strip 41. For this reason, with addition by conventional dropwise addition, a certain amount or more of extraction solution is temporarily added to the test strip, the extraction solution cannot completely absorb the test strip, and the extraction solution sometimes leaks, but by addition through the extraction solution guide 33 of the present invention, it is possible to prevent such leakage.

After introducing the extraction solution 6 into the testing means 4, in the present embodiment, a test was conducted by the usual lateral flow method. The test results could be confirmed from the judging window 44 of the housing 42. Further, the used test device 1 could be disposed of as is in the closed state shown in FIG. 2. Due to this, it is possible to dispose of the test device 1 in the state with the extraction solution 6 containing the specimen not leaking to the outside. In this way, according to the test device of the present invention, when testing a specimen which may include a virus or highly infectious bacteria etc., a specimen can be handled and treated efficiently.

Next, based on FIG. 1, FIG. 2, and FIG. 7, another method of use of the test device 1 according to the present embodiment will be explained. Note that, in FIG. 7, the specimen sampler 5 is omitted.

Figure 7A:
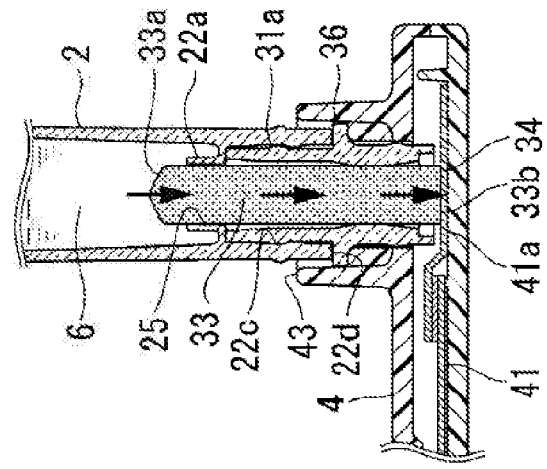

Another method of use of the test device 1 will be explained focusing on parts different from the above-mentioned method of use. When using the test device 1 of the present embodiment, as shown in FIG. 7A, before engaging the extraction container 2 and guiding member 3, the guiding member 3 may be inserted into the addition hole 43 of the housing 42 of the testing means 4 and the extraction solution outflow port 32 engaged. Specifically, if inserting the guiding member 3 into the addition hole 43, the projecting part 34 of the guiding member 3 abuts against the sample pad 41a of the test strip 41 of the testing means 4. If applying force in the direction from the extraction solution inflow port side to the testing means 4 side of the guiding member 31 so that the outflow port side engaging part 32a of the guiding member 3 fits into the addition hole side engaging part 43a of the addition hole 43, as shown in FIG. 7A, the operations (i) to (iii) occur: (i) the extraction solution guide 33 slides through the inside of the tube of the guiding member 3 to the extraction solution inflow port 31 side (top side), (ii) the flange part 36 of the guiding member 3 abuts against the guiding member support part 43b of the testing means 4 whereby the position in the vertical direction is determined, and (iii) the outflow port side engaging part 32a of the guiding member 3 and the addition hole side engaging part 43a of the testing means 4 engage and the guiding member 3 and the testing means 4 are connected in a closed manner.

Figure 7B:
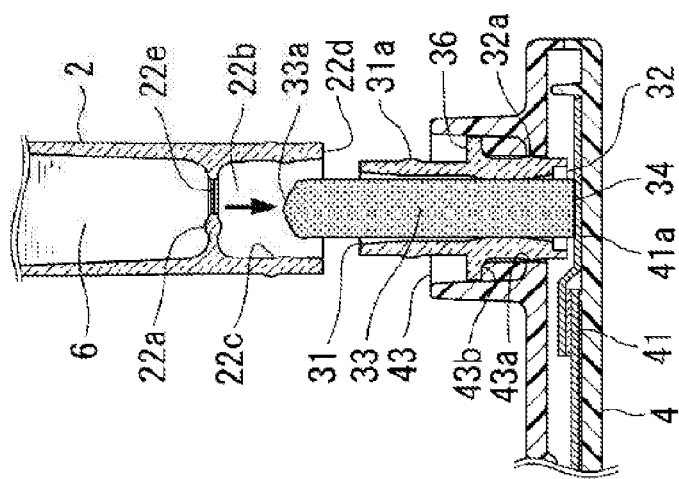

Next, as shown in FIG. 7B, the extraction solution inflow port 31 of the guiding member 3 connected with the testing means 4 is held in the holding region 22b of the bottom part 22 of the container 2. Specifically, it is attached so that the holding region 22b of the guiding member 3 covers the extraction solution inflow port 31.

Figure 7C:
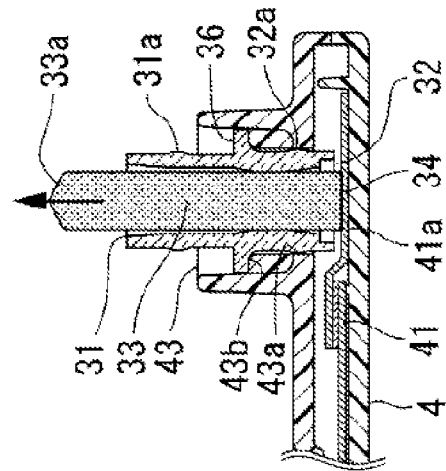

Next, as shown in FIG. 7C, if applying further force in the direction from the extraction container 2 side to the guiding member 3 side, the pointed end part 33a of the extraction solution guide 33 reaches the sealing part 22a of the extraction container 2 and this pointed end part 33a breaks the breaking part 22e of the sealing part 22a to form the through hole 25. Due to this, the extraction container 2 and the guiding member 3 are connected, and the extraction solution 6 which had been held in the extraction container 2 flows through the through hole 25 or the extraction solution guide 33 sticking out from the through hole 25 to the extraction solution inflow port 31 of the guiding member 3. Further, the end part 22d of the extraction container 2 abuts against the flange part 36 of the guiding member 3 and the bottom part side engaging part 22c of the extraction container 2 and the inflow port side engaging part 31a of the guiding member 3 are engaged. Due to this, the extraction container 2 and the guiding member 3 are connected in a sealed manner, so leakage of the extraction solution 6 flowing into the guiding member 3 can be prevented. The rest of the explanation relating to the method of use of the test device 1 is similar to the case of the above-mentioned method of use. The functions and actions and effects are also similar.

Next, referring to FIG. 8 and FIG. 9, a second embodiment of the present invention will be explained.

The test device 10 according to the second embodiment of the present invention is configured in the same way as the first embodiment except for differing partially from the test device 1 according to the first embodiment in the configurations of the bottom part 122 of the extraction container 20, the extraction solution inflow port 131 of the guiding member 30, and the addition hole 143 of the testing means 4. Note that, in the present embodiment, the same configurations as the first embodiment are explained using the same reference signs.

Figure 8A:
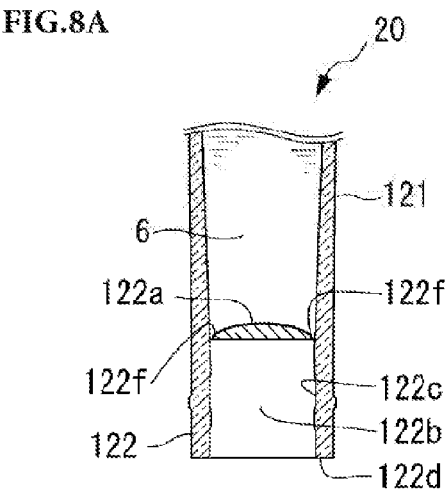

Based on FIG. 8A, the extraction container 20 in the present embodiment will be explained. The bottom part 122 of the extraction container 20 is provided with a sealing part 122a at a position a predetermined distance away from the end part 122d at the bottom part side. To enable the projecting tab part 131b provided at the extraction solution inflow port 131 of the guiding member 30 explained later to easily form the through hole 125, this sealing part 122a has a part which the projecting tab part 131b abuts against, in the present embodiment, at the circumferential end part of the sealing part 122a, a circular shaped breaking part 122f formed thinly at that part. Between the sealing part 122a and the end part 122d of the bottom part 122, a holding region 122b for holding the extraction solution inflow port 131 of the guiding member 30 is provided. At the inside wall of the holding region 122b, a bottom part side engaging part 122c is provided engaging with the inflow port side engaging part 131a provided at the outside wall of the extraction solution inflow port 131.

Figure 8B:
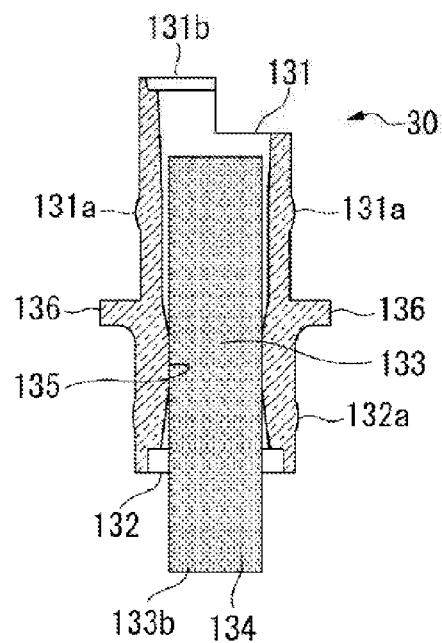

Next, based on FIG. 8B, the guiding member 30 in the present embodiment will be explained. The guiding member 30 is provided with a projecting tab part 131b at one end side of the extraction solution inflow port 131. By pushing in the guiding member 30 from the end part 122d of the extraction container 20 to the holding region 122b, the extraction solution inflow port 131 of the guiding member 30 is fit into the bottom part 122 of the extraction container 20 and the projecting tab part 131b is pushed through the breaking part 122f of the sealing part 122a of the extraction container 20 to form the through hole. Note that, to more reliably form the through hole, the projecting tab part 131b of the guiding member 30 is preferably provided with a thin part at the front end side and a thick part at the base end side (extraction solution inflow port side) whereby a step difference is formed between the thin part of the front end side and the thick part of the base end side. By being configured in this way, the step difference of the projecting tab part 131b abuts against the sealing part 122a of the extraction container 20 and causes that breaking part 122f etc. to deform, so a clearance is easily formed near the through hole 25 formed by this projecting tab part 131b. Due to this clearance, the extraction solution 6 quickly flows into the guiding member 30.

Figure 8C:
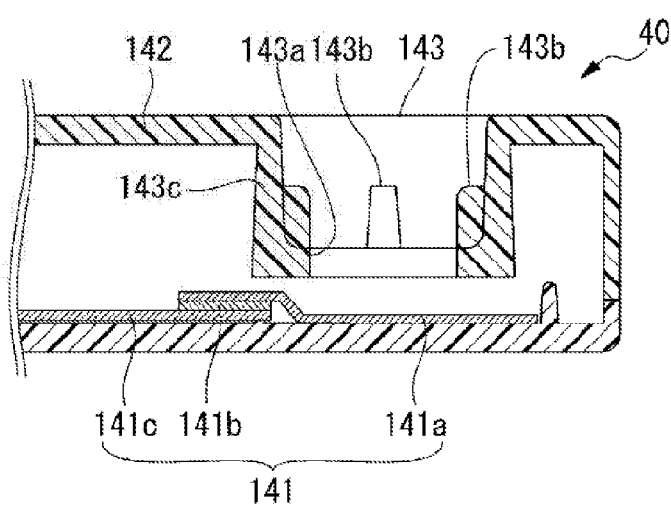

Next, based on FIG. 8C, the testing means 40 in the present embodiment will be explained. In the present embodiment, the surface of the housing 142 of the testing means 40 is provided with a substantially circular addition hole 143 for adding the extraction solution 6. In the present embodiment, unlike the above-mentioned first embodiment, the surface of the housing 142 at which the addition hole 143 is provided is configured flat. By designing the thickness (height) of the housing 142 large, an addition hole wall 143c or other engaging part is provided at the inside of the housing 142. For this reason, in the peripheral direction of the addition hole 243, an addition hole wall 143c formed substantially vertically downward (direction in which test strip 141 is held) is provided. This addition hole wall 143c is formed to support and fasten the guiding member 30 and can prevent leakage of the extraction solution 6. At the inside wall of the addition hole wall 143c, an addition hole side engaging part 143a is provided for stably maintaining the abutting state when inserting the extraction solution outflow port 131 of the guiding member 30 in the addition hole 143 and making the outflow port side end part 133b abut against the test strip 141. Specifically, the inside wall of the addition hole wall 143c is provided with a projecting addition hole side engaging part 143a continuously in the peripheral direction. This addition hole side engaging part 143a engages with the outflow port side engaging part 132a of the guiding member 30 and reliably fastens and connects the two. This addition hole side engaging part 143a may be any structure so long as a structure able to engage with the outflow port side engaging part 132a of the guiding member 30. For example, one or more projecting parts, recessed parts, projecting grooves, recessed grooves, or ribs running continuously in ring shapes in the peripheral direction, one or more projecting parts, recessed parts, projecting grooves, recessed grooves, or ribs running continuously in spiral shapes in the peripheral direction, or any combination of the same at the inside wall of the addition hole 143 may be mentioned.

Further, at the inside wall of the addition hole wall 143c at the top side (surface direction of housing 142) of the above-mentioned addition hole side engaging part 143a, four guiding member support parts 143b projecting out in the peripheral direction are provided at substantially equal intervals. The step parts of these guiding member support parts 143b support and fasten the above-mentioned flange part 136 of the guiding member 30 and determine the position in the vertical direction when the guiding member 30 abuts against the test strip 141 of the testing means 40. For this reason, the state of the projecting part 134 comprised of the extraction solution guide 133 of the guiding member 30 abutting against the test strip 141 can be maintained. In the present embodiment, the guiding member support parts 143b are configured from projecting step parts continuously extending in the upward direction from the addition hole side engaging part 143a, but the addition hole side engaging part 143a and the guiding member support parts 143b may also be separately formed. Further, by the flange part 136 of the guiding member 30 abutting against the guiding member support parts 143b of the addition hole 143, the guiding member 30 and the testing means 40 are further sealed and leakage of the extraction solution 6 can be prevented.

The rest of the explanation of the configurations of the extraction container 20, guiding member 30, and testing means 40 is similar to the case of the above-mentioned first embodiment. The functions and actions and effects are also similar. Further, the configuration of the specimen sampler 5 forming the test device 10 as well is similar to the case of the above-mentioned first embodiment. The functions and actions and effects are also similar.

Next, based on FIG. 9, the method of use of the test device 10 according to the present embodiment will be explained. Note that, in FIG. 9, the specimen sampler 5 is omitted.

Figure 9A:
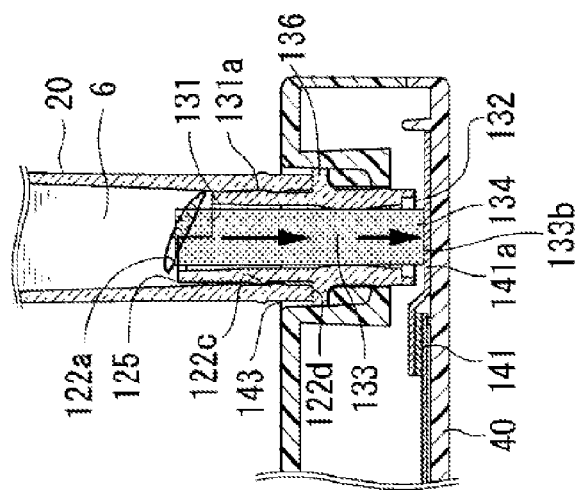

In using the test device 10, the specimen sampler 5 samples a specimen, the specimen is suspended inside the extraction solution 6 inside the extraction container 20, then, as shown in FIG. 9A, the extraction solution inflow port 131 side of the guiding member 30 is pushed into the holding region 122b of the bottom part 122 of the extraction container 20 to attach it. At this stage, the extraction container 20 and the guiding member 30 are not connected and are in the temporarily fit state.

Figure 9B:
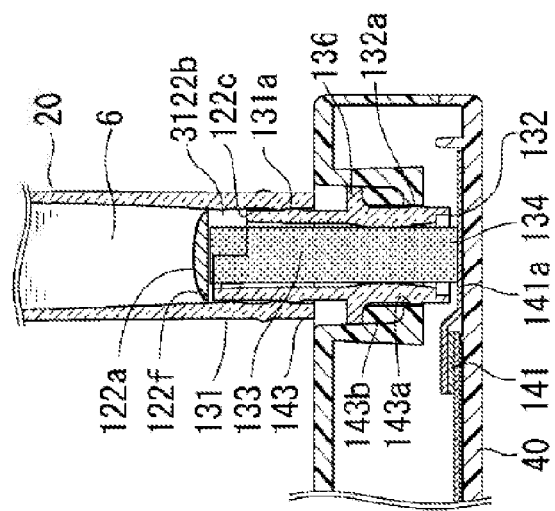

Next, as shown in FIG. 9B, the extraction solution outflow port 132 side of the guiding member 30 temporarily fit into the extraction container 20 is inserted into the addition hole 143 of the housing 142 of the testing means 40. If gripping the barrel part of the extraction container 20 and inserting the guiding member 30 to the inside of the addition hole 143, the outflow port side end part 133b of the guiding member 30 abuts against the sample pad 141a of the test strip 141 of the testing means 4. Furthermore, if applying force in the direction from the extraction container 20 side to the testing means 40 side, as shown in FIG. 9B, the operations (i) to (iii) occur: (i) the extraction solution guide 133 slides through the inside of the tube of the guiding member 30 to the extraction solution inflow port 131 side (top side), (ii) the outflow port side engaging part 132a of the guiding member 30 and the addition hole side engaging part 143a of the testing means 40 engage and the guiding member 30 and the testing means 40 are connected in a closed manner, and (iii) the flange part 136 of the guiding member 30 abuts against the guiding member support part 143b of the testing means 40 whereby the position in the vertical direction is determined.

Figure 9C:
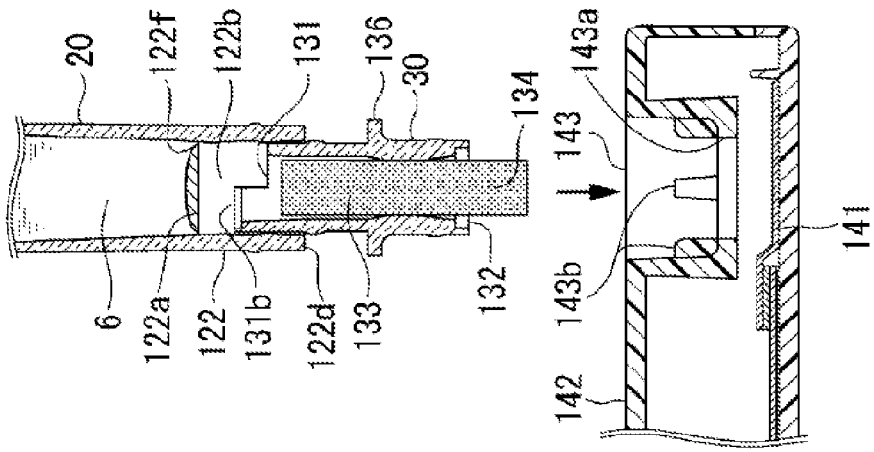

As shown in FIG. 9C, furthermore, if applying force in the direction from the barrel part side to the testing means 40 side of the extraction container 20, the breaking part 122f of the sealing part 122a of the extraction container 20 is pushed against by the projecting tab part 131b provided at the extraction solution inflow port 131 and the projecting tab part 131b breaks the breaking part 122f to form the through hole 125. Due to this, the extraction container 20 and guiding member 30 are connected and the extraction solution 6 held in the extraction container 20 flows through the through hole 125 to flow into the extraction solution inflow port 131 of the guiding member 30. Further, the end part 122d of the extraction container 20 abuts against the flange part 136 of the guiding member 30 and the bottom part side engaging part 122c of the extraction container 20 and the inflow port side engaging part 131a of the guiding member 30 engage. Due to this, the extraction container 20 and the guiding member 30 are connected in a sealed manner, so it is possible to prevent leakage of the extraction solution 6 flowing into the extraction solution inflow port 131 to the outside environment. The extraction solution 6 flowing into the extraction solution inflow port 131 is absorbed in the extraction solution guide 133 held inside the tube of the guiding member 30 and moves by capillary action to the outflow port side end part 133b of the extraction solution guide 133. The outflow port side end part 133b of the extraction solution guide 133 abuts against the sample pad 141a of the test strip 141 of the testing means 40, so the extraction solution 6 passes through the outflow port side end part 133b of the guiding member 30 and moves to the sample pad 141a. In this way, rather than adding the extraction solution 6 dropwise, it is possible to simply and reliably introduce the extraction solution 6 to the test strip 141 in a sealed manner.

Next, based on FIG. 10, another method of use of the test device 10 according to the present embodiment will be explained. Note that, in FIG. 10, the specimen sampler 5 is omitted.

Figures 10A, 10B:
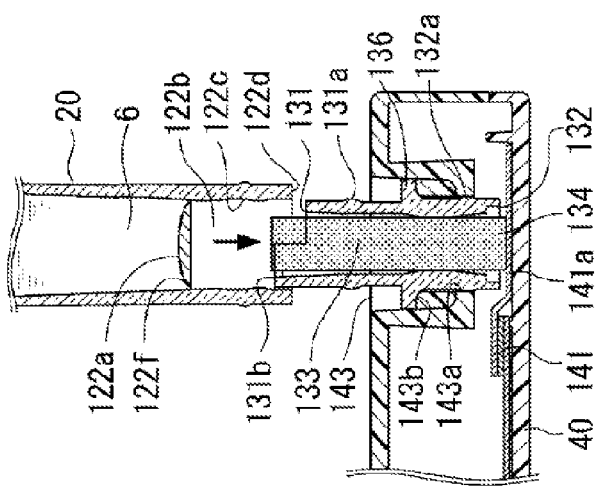

The other method of use of the test device 10 will be explained focusing on parts different from the above method of use. When using the test device 10 in the present embodiment, as shown in FIG. 10A, before engaging the extraction container 20 and the guiding member 30, the guiding member 30 may be inserted inside of the addition hole 143 of the housing 142 of the testing means 40 and made to engage with the extraction solution outflow port 132. Specifically, if inserting the guiding member 30 into the addition hole 143, the outflow port side end part 133b of the guiding member 30 abuts against the sample pad 141a of the test strip 141 of the testing means 40. Therefore, if applying force in the direction from the extraction solution inflow port side to the testing means 40 side of the guiding member 131 so that the outflow port side engaging part 132a of the guiding member 30 fits into the addition hole side engaging part 143a of the addition hole 143, as shown in FIG. 10A, the operations (i) to (iii) occur: (i) the extraction solution guide 133 slides through the inside of the tube of the guiding member 30 to the extraction solution inflow port 131 side (top side), (ii) the flange part 136 of the guiding member 30 abuts against the guiding member support part 143b of the testing means 40 whereby the position in the vertical direction is determined, and (iii) the outflow port side engaging part 132a of the guiding member 30 and the addition hole side engaging part 143a of the testing means 40 engage and the closed connection state of guiding member 30 and the testing means 40 is fixed.

Next, as shown in FIG. 10B, the extraction solution inflow port 131 of the guiding member 30 connected with the testing means 40 is held in the holding region 122b of the bottom part 122 of the container 20. Specifically, it is attached by pushing it in so that the holding region 122b of the guiding member 30 covers the extraction solution inflow port 131.

Figure 10C:
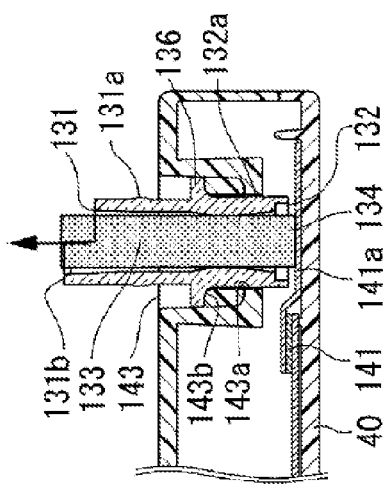

Next, as shown in FIG. 10C, if applying further force in the direction from the extraction container 20 side to the guiding member 30 side, the projecting tab part 131b provided at the extraction solution inflow port 131 of the guiding member 30 pushes against the breaking part 122f of the sealing part 122a of the extraction container 20 and breaks through it to form a through hole 125 in the sealing part 122a. Due to this, the extraction container 20 and the guiding member 30 are connected and the extraction solution 6 held in the extraction container 20 flows through the through hole 125 to the extraction solution inflow port 131 of the guiding member 30. Further, the end part 122d of the extraction container 20 abuts against the flange part 136 of the guiding member 30, and the bottom part side engaging part 122c of the extraction container 20 and the inflow port side engaging part 131a of the guiding member 30 engage. Due to this, the extraction container 20 and the guiding member 30 are connected in a sealed manner, so leakage of the extraction solution 6 flowing into the guiding member 30 to the outside environment can be prevented. The rest of the explanation relating to the method of use of the test device 10 is similar to the case of the method of use of the above-mentioned first embodiment. The functions and actions and effects are also similar.

Next, referring to FIG. 11 and FIG. 12, a third embodiment of the present invention will be explained.

The test device 100 according to the third embodiment of the present invention is configured similar to the first embodiment except for partially differing from the test device 1 according to the first embodiment in the configurations of the open part 223 and bottom part 222 of the extraction container 200, the extraction solution inflow port 231 of the guiding member 300, and the addition hole 243 of the testing means 400.

Based on FIG. 11A, the extraction container 200 will be explained. The extraction container 200 in the present embodiment has a barrel part 221, a bottom part 222 sealing one end side of the barrel part 221 in the axial direction, and an open part 223 opening at the other end side. In the present embodiment, the extraction container 200 and the guiding member 300 are connected through the open part 223 of the extraction container 200, so the bottom part 222 of the extraction container 200, unlike the other embodiments, is not formed so that a through hole etc. can be fainted. On the other hand, at the inside wall near the open part 223, an open part side engaging part 223a engaging with the inflow port side engaging part 231a provided at the outside wall of the extraction solution inflow port 231 of the guiding member 300 explained later is provided. In the present embodiment, as shown in FIG. 11A, as the open part side engaging part 223a, a recessed part continuous running along the peripheral direction at the inside wall near the open part 223 is provided. This open part side engaging part 223a may be any structure so long as a structure able to engage with the inflow port side engaging part 231a of the guiding member 300. For example, one or more projecting parts, recessed parts, projecting grooves, recessed grooves, or ribs running continuously in ring shapes in the peripheral direction, one or more projecting parts, recessed parts, projecting grooves, recessed grooves, or ribs running continuously in spiral shapes in the peripheral direction, or any combination of the same at the inside wall or outside wall near the open part 223 may be mentioned.

Next, based on FIG. 11B, the guiding member 300 will be explained. The guiding member 300 in the present embodiment has an extraction solution inflow port 231 at one end side, has an extraction solution outflow port 232 at the other end side, and holds the extraction solution guide 233 at the inside. The extraction solution inflow port 231 is formed so as to be able to engage with the open part 223 of the extraction container 200 in a sealed manner. The outside wall of the extraction solution inflow port 231 is provided with an inflow port side engaging part 231a engaging with the open part side engaging part 223a of the extraction container 2. In the present embodiment, as shown in FIG. 11B, as the inflow port side engaging part 231a, a projecting part continuously running along the peripheral direction at the outside wall near the extraction solution inflow port 231 is provided. This inflow port side engaging part 231a engages with the open part side engaging part 223a of the extraction container 200 as explained above and reliably fastens and connects the two in a sealed manner. This inflow port side engaging part 231a may be any structure so long as a structure able to engage with the open part side engaging part 223a of the extraction container 200. For example, one or more projecting parts, recessed parts, projecting grooves, recessed grooves, or ribs running continuously in ring shapes in the peripheral direction, one or more projecting parts, recessed parts, projecting grooves, recessed grooves, or ribs running continuously in spiral shapes in the peripheral direction, or any combination of the same at the inside wall or outside wall of the extraction solution inflow port 231 may be mentioned.

Further, the outside wall of the tube of the guiding member 300 is formed with a flange part 237 along the peripheral direction. This flange part 236 is supported by a guiding member support part 243b provided at the top end part of the addition hole wall 243c of the addition hole 243 of the later explained testing means 400 and functions to hold the abutting state when the projecting part 234 comprised of the extraction solution guide 233 abuts against the testing means 400. For this reason, the capillary action of the extraction solution guide 233 stably functions and the extraction solution 6 is efficiently added to the testing means 400. Furthermore, when the extraction solution outflow port 232 of the guiding member 300 is inserted into the addition hole 243 of the testing means 400, the guiding member support part 243b abuts against this flange part 236 and is sealed, so the guiding member 300 and the testing means 400 are connected in a sealed manner and leakage of the extraction solution 6 to the outside environment can be prevented.

Inside the tube connecting the above-mentioned extraction solution inflow port 231 and extraction solution outflow port 232, a rod-shaped extraction solution guide 233 is held. In the present embodiment, the extraction solution guide 233 is formed into a substantially circular columnar shape. The outflow port side end part 233b of the extraction solution guide 233 at the extraction solution outflow port 232 side forms the projecting part 234 arranged so as to stick out from the extraction solution outflow port 232. The extraction solution guide 233 is anchored by the guide holding part 235 provided inside the tube and is arranged so as to not detach from the inside of the tube of the guiding member 300, but is designed so as to be able to slide through the inside of the tube when force is applied from the extraction solution outflow port 232 side to the extraction solution inflow port 231 side. In the present embodiment, the guide holding part 235 is formed into a projecting shape continuously running along the peripheral direction at the inside wall of the tube of the guiding member 300. The part of the guide holding part 235 becomes slightly narrower in inside diameter of the tube. In this way, the guide holding part 235 is configured so as to anchor the extraction solution guide 233 inside the tube of the guiding member 300 to an extent whereby the extraction solution guide 233 can slide inside the tube when a certain force is applied to the outflow port side end part 233b. In the present embodiment, the extraction solution guide 233 does not require the function of forming a through hole, so the end part of the extraction solution guide 233 is configured substantially flat at the two end parts. However, if possible to make the extraction solution 6 move to the testing means 400, any shape will be possible.

Next, based on FIG. 11C, the testing means 400 will be explained. In the present embodiment, the surface of the housing 242 of the testing means 400 is provided with an addition hole 243 for adding the extraction solution 6. The addition hole 243 has an addition hole wall 243c formed substantially vertically in the peripheral direction of the hole and is formed so as to be able to support and fasten the guiding member 300 and prevent leakage of the extraction solution 6. At the inside wall of the addition hole wall 243c, an addition hole side engaging part 243a is provided for stably maintaining the abutting state when inserting the extraction solution outflow port 231 of the guiding member 300 in the addition hole 243 and making the outflow port side end part 233b abut against the test strip 241. Specifically, at the inside wall of the addition hole wall 243c, a recessed addition hole side engaging part 243a is continuously provided in the peripheral direction. This addition hole side engaging part 243a engages with the outflow port side engaging part 232a of the guiding member 300 to reliably fasten and connect the two. This addition hole side engaging part 243a may be any structure so long as a structure able to engage with the outflow port side engaging part 232a of the guiding member 300. For example, one or more projecting parts, recessed parts, projecting grooves, recessed grooves, or ribs running continuously in ring shapes in the peripheral direction, one or more projecting parts, recessed parts, projecting grooves, recessed grooves, or ribs running continuously in spiral shapes in the peripheral direction, or any combination of the same at the inside wall or outside wall of the addition hole 243 may be mentioned.

Further, the top end part of the above-mentioned addition hole wall 243c acts as a guiding member support part 243b, supports and fastens the flange part 236 of the above-mentioned guiding member 300, and determines the position in the vertical direction when abutting against the test strip 241 of the testing means 400 of the guiding member 300. For this reason, when the projecting part 234 comprised of the extraction solution guide 233 of the guiding member 300 abut against the test strip 241, it is possible to maintain the state where the outflow port side end part 233b abuts against the test strip 241. Further, by the flange part 236 of the guiding member 300 abutting against the guiding member support part 243b of the addition hole 243, the guiding member 300 and the testing means 400 are sealed and leakage of the extraction solution 6 can be prevented.

The rest of the explanation regarding the configurations of the extraction container 200, guiding member 300, and testing means 400 is similar to the case of the above-mentioned first embodiment. The functions and actions and effects are also similar. Further, the configuration of the specimen sampler 5 forming the test device 100 is also similar to the case of the above-mentioned first embodiment. The functions and actions and effects are also similar.

Next, based on FIG. 12, the method of use of the test device 100 according to the present embodiment will be explained. Note that, in FIG. 12, the specimen sampler 5 is omitted.

Figure 12A:
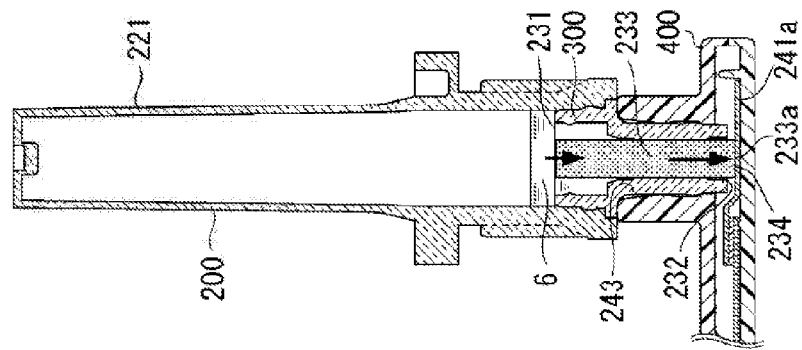
Figure 12B:
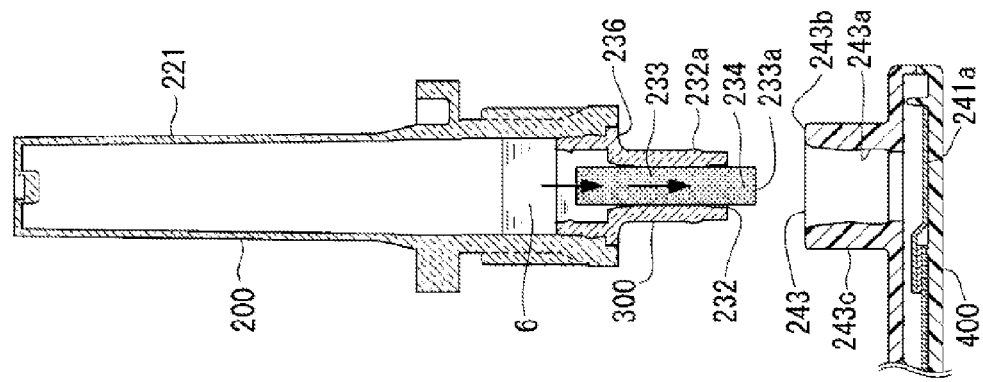

In using the test device 10, the specimen sampler 5 samples a specimen, and the specimen is suspended inside the extraction solution 6 inside the extraction container 200. Note that, in the present embodiment, to attach the guiding member 300 at the open part 223 of the extraction container 200, the extraction container 200 does not hold a specimen sampler 5 provided with the cap part 5, but it may also hold a specimen sampler not having a cap part 5. Next, as shown in FIG. 12A, the extraction solution inflow port 231 of the guiding member 300 is pushed into the open part 223 of the extraction container 200 to engage them. Due to this, the open part side engaging means 231 of the extraction container 200 and the inflow port side engaging means 231 of the guiding member 300 engage and the extraction container 200 and the guiding member 300 are connected and communicated in a sealed manner. Since the extraction container 200 and the guiding member 300 are connected in a sealed manner in this way, leakage of the extraction solution 6 flowing into the extraction solution inflow port 231 to the outside environment can be prevented. Next, as shown in FIG. 12B, if turning the extraction solution outflow port 232 of the guiding member 300 in the downward direction, the extraction solution 6 stored in the extraction container 200 flows into the extraction solution inflow port 231 of the guiding member 300. The extraction solution 6 flowing into the extraction solution inflow port 231 is absorbed by the extraction solution guide 233 held inside the tube of the guiding member 300 and moved by capillary action to the outflow port side end part 233b of the extraction solution guide 233.

Figure 12C:
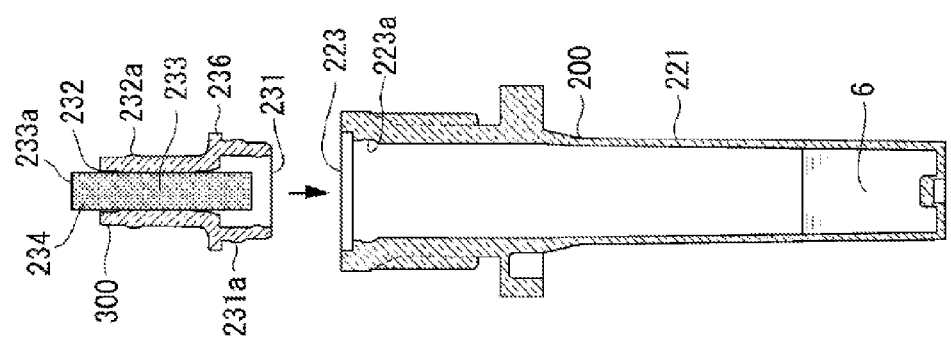

Next, as shown in FIG. 12C, if inserting the extraction solution outflow port 232 of the guiding member 300 connected to the extraction container 200 into the addition hole 243, the outflow port side end part 233b of the guiding member 300 abuts against the sample pad 241a of the test strip 241 of the testing means 400. Due to this, the extraction solution 6 simply moves to the sample pad 241a through the outflow port side end part 233b of this guiding member 300. In this way, rather than adding the extraction solution 6 dropwise, it is possible to simply and reliably introduce the extraction solution 6 to the test strip 241 in a closed manner. Further, by applying force in the direction from the extraction container 200 side to the testing means 400 side to fit it in, (i) the flange part 236 of the guiding member 300 abuts against the guiding member support part 243b of the testing means 400 whereby the position in the vertical direction is fixed and (ii) the outflow port side engaging part 232a of the guiding member 300 and the addition hole side engaging part 243a of the testing means 400 engage whereby the closed connected state of the guiding member 300 and testing means 400 is fixed. Due to this, the testing means 400 and guiding member 300 are connected in a sealed manner and extraction solution is added to the testing means without the extraction solution 6 leaking to the outside environment. The rest of the explanation relating to the method of use of the test device 100 is similar to the case of the method of use of the first embodiment explained above. The functions and actions and effects are also similar.

Next, referring to FIG. 13 and FIG. 14, a fourth embodiment of the present invention will be explained.

The test device 101 according to the fourth embodiment of the present invention is configured similar to the third embodiment except for partially differing from the test device 100 according to the third embodiment in the structure of the inside wall of the tube member, including the guide holding part 335 of the guiding member 301, and the structure of the addition hole 343 of the testing means 401.

First, based on FIG. 13, the guiding member 301 will be explained. The guiding member 301 in the present embodiment has an extraction solution inflow port 331 at one end side, has an extraction solution outflow port 332 at the other end side, and holds the extraction solution guide 333 at the inside. Further, at the outside wall of the tube member of the guiding member 301, a flange part 336 is formed along the peripheral direction. In the present embodiment, when the open part 223 of the extraction container 200 and the extraction solution inflow port 331 of the guiding member 301 engage, the top side of this flange part 336 (extraction container 200 direction) and step part provided at the open part of the extraction container 200 abut and the extraction container 200 and guiding member 301 connect in a more sealed manner, so the flange part 336 plays the role of preventing leakage of the extraction solution 6 to the outside environment.

Figure 13A:
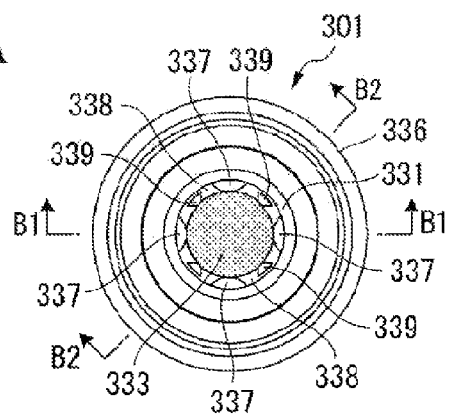
Figure 13B:
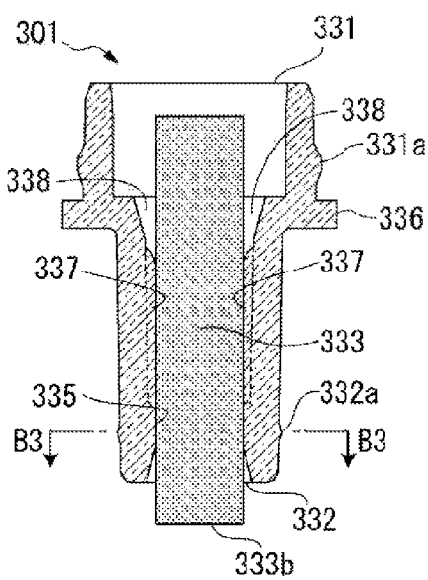
Figure 13C:
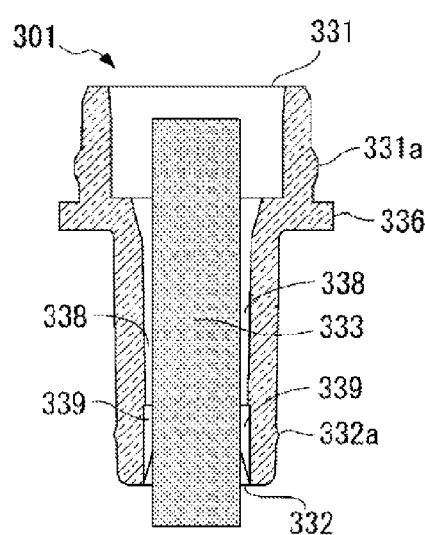
Figure 13D:
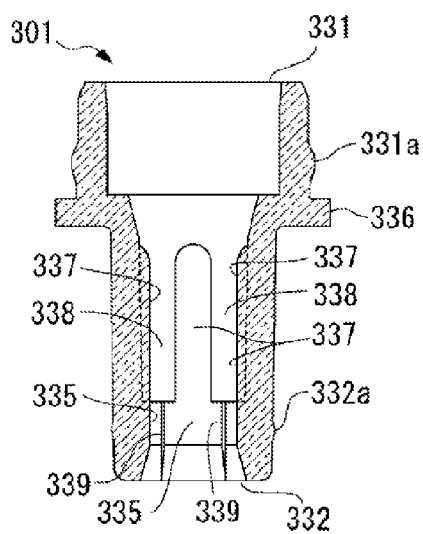

In the tubular member of the guiding member 301 between the extraction solution inflow port 331 and the extraction solution outflow port 332, a rod-shaped extraction solution guide 333 is held. The extraction solution guide 333 is anchored by the guide holding part 335 and guide support parts 337 provided inside the tube and is arranged so as not to detach from inside the tube of the guiding member 301, but is designed to be able to slide inside the tube when force is applied from the extraction solution outflow port 332 side to the extraction solution inflow port 331 side. As shown in FIGS. 13B to 13E, in the present embodiment, the guide holding part 335 is formed in a projecting shape continuously running along the peripheral direction at the inside wall of the tube at the extraction solution outflow port 332 of the guiding member 301. For this reason, at the guide holding part 335, the tube inside diameter is narrowed a bit so as to enable the extraction solution guide 333 to be held by being pressed from its circumference. Furthermore, in the present embodiment, as shown in FIGS. 13A, 13B, and 13D, the guide support parts 337 are formed as projecting curves formed along the inside wall of the tube of the top side from the guide holding part 335 (extraction solution inflow port 331 side). Four projecting curves are provided at constant intervals in the peripheral direction. As shown in FIGS. 13A and 13B, the extraction solution guide 333 is supported by four projecting curves of the guide support parts 337. Due to this, wobbling at the extraction solution inflow port 331 side of the extraction solution guide 333 held inside the guiding member 301 is suppressed and the extraction solution guide 333 can be stably anchored. Further, when the extraction solution guide 333 slides inside the tube of the guiding member 301, the projecting curves of the guide support parts 337 guide the sliding direction, so the extraction solution guide 333 is slid along the approximately center axis. The guide support parts 337 may be any structures so long as structures able to support the extraction solution guide 333. For example, projecting flat surfaces, projecting grooves, or all sorts of shapes provided at predetermined intervals in the peripheral direction or continuous projecting parts and other structures in a ring shape along the peripheral direction at the inside wall of the tube of the guiding member 301 may be mentioned.

Figure 13E:
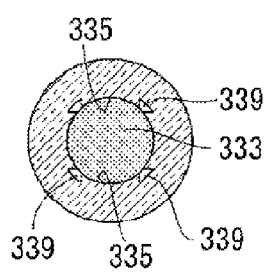

Furthermore, in the present embodiment, as shown in FIGS. 13A, 13D, and 13E, the guide holding part 335 of the guiding member 301 is provided with air circulation grooves 339 for circulating air to the extraction solution guide 333. Due to this, air is supplied to the extraction solution guide 333 and the pressure inside the extraction solution guide 333 is adjusted, so absorption by the extraction solution guide 333 of the extraction solution 6 and movement of the extraction solution 6 to the detecting means 401 can be performed efficiently. In the present embodiment, the air circulation grooves 339, as shown in FIGS. 13A, 13D, and 13E, are formed at the guide holding part 335 at the bottom sides of the clearances 338 where the guide support parts 337 are not formed (extraction solution outflow port 332 side) as recessed grooves having substantially triangular shaped cross-sections and extending in the substantially vertical direction. Four are provided at constant intervals in the peripheral direction. The air circulation grooves 339, as shown in FIGS. 13A and 13E, are shaped with the vertex parts of the substantially triangular shapes slightly cut away. At the cut away vertex parts, the extraction solution guide 333 is connected. The widths of the grooves of the parts connecting with the extraction solution guide 333 are designed so that the air circulation grooves 339 do not permit drops of the extraction solution 6 from entering inside of the air circulation grooves 339 and substantially allow only the flow of air. Specifically, more preferably 0.19 mm to 0.22 mm. The air circulation grooves 439 are connected with the clearance parts 338 where the guiding member support parts 337 are not provided. Air flowing in from the extraction solution outflow port 332 side through the air circulation grooves 339 is supplied to the extraction solution guide 333 or flows through the clearances 338 to the extraction solution inflow port 331 side. Due to this, the extraction solution 6 smoothly moves through the extraction solution guide 333 to the detecting means 401. Note that, the air circulation grooves 339 may be any structures so long as structures not allowing drops of the extraction solution 6 to enter the grooves and substantially allowing flow of only air. For example, in a plane view, substantially polygonal shapes, substantially circular shapes, substantially fan shapes, or indefinite shaped grooves or pluralities of ribs etc. may be mentioned.

Next, based on FIG. 14, the testing means 401 will be explained. At the top surface of the housing 342 of the testing means 401, an addition hole 343 for adding an extraction solution 6 is provided. The addition hole 343 has an addition hole wall 343c formed substantially vertically in the peripheral direction of the hole and is formed so as to support and fasten the guiding member 301 and so as to prevent leakage of the extraction solution 6. At the inside wall of the addition hole wall 343c, there is provided an addition hole side engaging part 343a for stably holding the state when inserting the extraction solution outflow port 332 of the guiding member 301 in the addition hole 343 and making the outflow port side end part 333b abut against the test strip 341. Specifically, at the inside wall of the addition hole wall 343c, a recessed addition hole side engaging part 343a is continuously provided in the peripheral direction. This addition hole side engaging part 343a engages with the outflow port side engaging part 332a of the guiding member 301 whereby the two are reliably fastened and connected. Further, at the inside wall at the bottom side of the above-mentioned addition hole side engaging part 343a (bottom direction of addition hole 343), a ring shaped guiding member support part 343b continuously sticking out in the peripheral direction is provided. As shown in FIG. 14B, the end part of the above-mentioned guiding member 301 at the extraction solution outflow port 332 side abuts against the top surface of this guiding member support part 343b whereupon the guiding member 301 is supported and fastened by the detecting means 401.

Figure 14A:
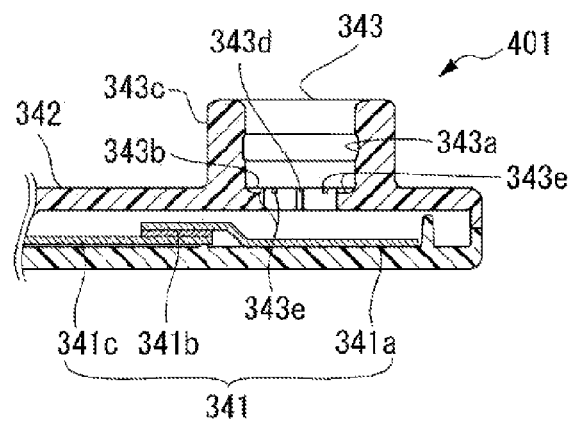
FIG. 14A is an enlarged partial cross-sectional view showing a testing means of a test device according to the fourth embodiment of the present invention and FIG. 14B is an explanatory view schematically showing the state of use of the test device according to the fourth embodiment of the present invention.
Figure 14B:
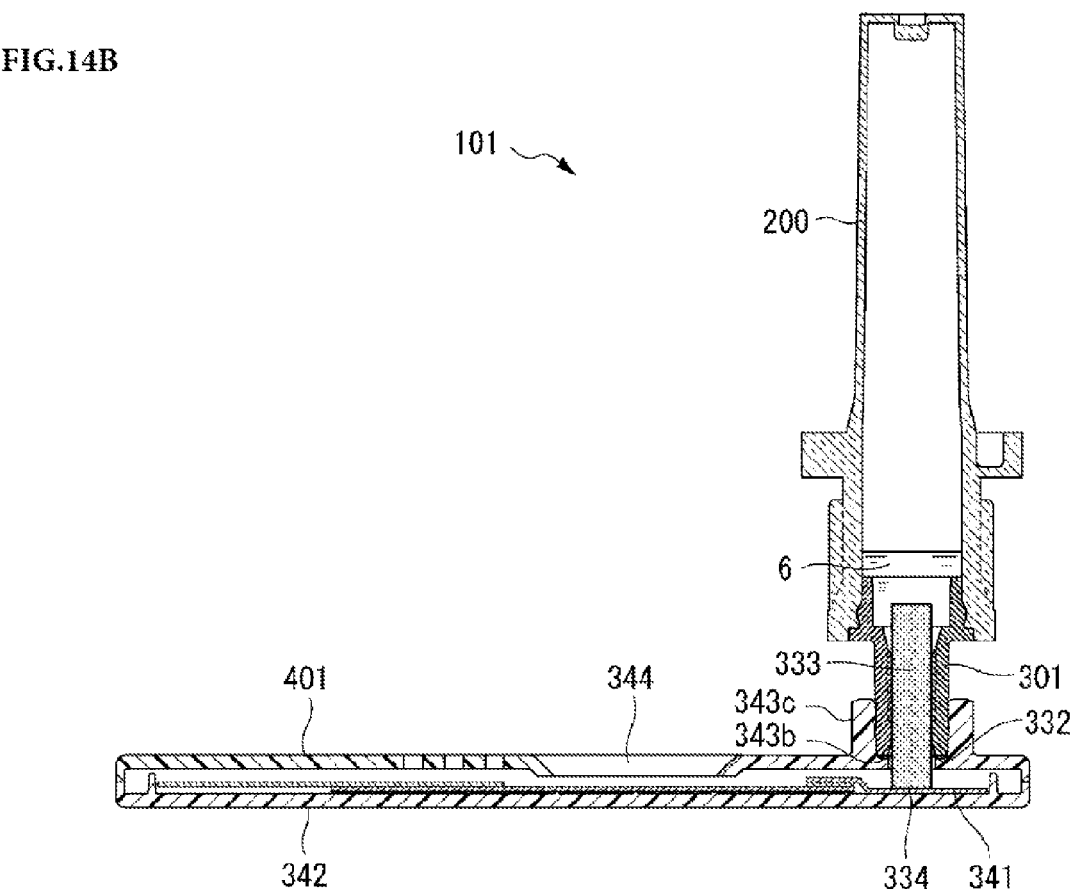

Furthermore, in the present embodiment, as shown in FIG. 14A, the guiding member support part 343b of the addition hole 343 is provided with slits 343d and addition hole side grooves 343e for circulating air to the inside of the tube of the guiding member 301. Due to this, air is fed to the extraction solution guide 333 and the pressure inside the extraction solution guide 333 is adjusted, so the absorption of the extraction solution 6 by the extraction solution guide 333 and movement of the extraction solution 6 to the detecting means 401 can be performed more efficiently. In the present embodiment, the slits 343*d* are fouled by making fine cuts running through the vertical direction in the guiding member support part 343*b* fouled in a ring shape. Two are provided at positions facing each other across the addition hole 343. Further, the addition hole side grooves 343*e* are fouled as recessed grooves fouled in the guiding member support part 343*b*. Six recessed grooves were provided in a radial manner in the surface of the guiding member support part 343*b* fouled in a recessed ring shape. Due to this, in the guiding member 301 engaging with the addition hole 343 of the detecting means 401 in a sealed manner, clearances are fouled enabling air to flow between the guiding member support part 343*b* of the detecting means 401 and the extraction solution outflow port 332 side of the guiding member 301. For this reason, air flowing through the slits 343*d* and addition hole side grooves 343*e* to the outflow port 332 side of the guiding member 301 is supplied to the extraction solution guide 333 or flows to the extraction solution inflow port 331 side. Due to this, the extraction solution 6 smoothly moves through the extraction solution guide 333 to the detecting means 401. Note that, the slits 343*d* may be any structure so long as structures substantially enabling circulation of air. For example, they may also be through holes etc. formed on the guiding member support part 343*b*. Similarly, the addition hole side grooves 343*e* may also be recessed parts fouled into ring shapes etc.

The rest of the explanation regarding the configuration and method of use of the guiding member 301 and testing means 401 is similar to the case of the above-mentioned third embodiment. The functions and actions and effects are also similar. Further, the configuration and method of use of the extraction container 200 and specimen sampler 5 forming the test device 101 are also similar to the case of the above-mentioned third embodiment. The functions and actions and effects are also similar.

Next, referring to FIG. 15 and FIG. 16, a fifth embodiment of the present invention will be explained.

The test device 102 according to the fifth embodiment of the present invention is configured similar to the first embodiment other than partially differing from the test device 1 according to the first embodiment in the structure of the inside wall of the tubular member including the guide holding part 335 of the guiding member 302 and the configuration of the addition hole 443 of the testing means 401.

Based on FIG. 15, the guiding member 302 will be explained. The guiding member 302 in the present embodiment holds an extraction solution guide 433 having an extraction solution inflow port 431 at one end side, having an extraction solution outflow port 432 at the other end side, and having a pointed end part 433*a* at the inside. Further, at the outside wall of the tubular member of the guiding member 302, a flange part 436 is formed along the peripheral direction. In the present embodiment, when the extraction solution inflow port 431 of the guiding member 302 is fit into the holding region 22*b* of the bottom part 22 of the extraction container 2, the end part 22*d* of the extraction container 2 abuts against the top side of the flange part 436 (extraction container 2 direction) and the extraction container 2 and guiding member 302 are connected in a sealed manner so this flange part 436 plays the role of preventing leakage of the extraction solution 6 to the outside environment.

Inside the tube connecting the extraction solution inflow port 431 and the extraction solution outflow port 432 of the guiding member 302, an extraction solution guide 433 is held. The extraction solution guide 433 is anchored by the guide holding part 435 and guide support part 437 provided inside the tube and is arranged so that it does not detach from the inside of the tube of the guiding member 302. The guide is designed to be able to slide inside the cylinder when force is applied from the extraction solution outflow port 432 side to the extraction solution inflow port 431 side. As shown in FIGS. 15B to 15D, in the present embodiment, the guide holding part 435 is formed into a projecting shape continuously running along the peripheral direction at the inside wall of the tube at the extraction solution outflow port 432 side of the guiding member 302. For this reason, the guide holding part 435 becomes narrower in tube inside diameter so as to be able to hold the extraction solution guide 433 while pressing against it from the surroundings. Furthermore, in the present embodiment, as shown in FIGS. 15A, 15B, 15D, and 15E, the guide support part 437 is formed as a projecting curved surface formed along the inside wall of the tube at the position (extraction solution inflow port 431 side) at the top side from the guide holding part 435. Four of the projecting curved surfaces are provided at constant intervals. As shown in FIGS. 15A and 16B, the extraction solution guide 433 is supported by four projecting curves of the guide support part 437. Due to this, wobbling at the extraction solution inflow port 431 side of the extraction solution guide 433 held inside the guiding member 302 is suppressed and the extraction solution guide 433 is stably anchored. Further, when the extraction solution guide 433 slides inside the tube of the guiding member 302, the projecting curve of the guide support part 437 guides the sliding direction, so the extraction solution guide 433 slides along the substantially center axis. The guide support part 437 may be any structure so long as a structure able to support the extraction solution guide 433. For example, projecting flat surfaces, projecting grooves, and all sorts of shapes of projecting parts provided at predetermined intervals in the peripheral direction or projecting parts or other structures continuously running in ring shapes along the peripheral direction at the inside wall of the tube of the guiding member 302 may be mentioned.

Furthermore, in the present embodiment, as shown in FIG. 15A and FIGS. 15D to 15F, at the guide holding part 435 of the guiding member 302, air circulation grooves 439 for circulating air to the extraction solution guide 433 are provided. Due to this, air is supplied to the extraction solution guide 433 and the pressure at the inside of the extraction solution guide 433 is adjusted, so absorption by the extraction solution guide 433 of the extraction solution 6 and movement of the extraction solution 6 to the detecting means 401 are performed more efficiently. In the present embodiment, the air circulation grooves 439, as shown in FIG. 15A and FIGS. 15D to 15F, are provided at the guide holding part 435 below the clearances 438 where the guide support parts 437 are not fouled (extraction solution outflow port 432 side) as recessed grooves having substantially triangular shaped cross-sections and extending in the substantially vertical direction. Four are provided at constant intervals in the peripheral direction. The air circulation grooves 439, as shown in FIGS. 15A and 15F, are shaped with the vertex parts of the substantially triangular shapes slightly cut away. At the cut away vertex parts, the extraction solution guide 433 is connected. The widths of the grooves of the parts connecting with the extraction solution guide 433 are designed so that the air circulation grooves 439 do not permit drops of the extraction solution 6 from entering inside of the air circulation grooves 439 and substantially allow only the flow of air. Specifically, the widths of the grooves of the air circulation grooves 439 at the sides connected with the extraction solution guide 433 are preferably 0.15 mm to 0.25 mm, more preferably 0.19 mm to 0.22 mm. The air circulation grooves 439 are connected with the clearance parts 438 where the guiding member support parts 437 are not provided. Air flowing in from the extraction solution outflow port 432 side through the air circulation grooves 439 is supplied to the extraction solution guide 433 or flows through the clearances 438 to the extraction solution inflow port 431 side. Due to this, the extraction solution 6 smoothly moves through the extraction solution guide 433 to the detecting means 401. Note that, the air circulation grooves 439 may be any structures so long as structures not allowing drops of the extraction solution 6 to enter the grooves and substantially allowing flow of only air. For example, in a plane view, substantially polygonal shapes, substantially circular shapes, substantially fan shapes, or indefinite shaped grooves or pluralities of ribs etc. may be mentioned.

Furthermore, in the present embodiment, as shown in FIGS. 15A to 15E, at the clearance 438 parts not formed with the guide support parts 437 of the inside wall of the inside of the tube of the guiding member 302, air guide grooves 440 for further circulating air to the extraction solution guide 433 are provided. Due to this, inside the tube of the guiding member 302, air is circulated at the clearance 438 parts, so absorption by the extraction solution guide 433 of the extraction solution 6 and movement of the extraction solution 6 to the detecting means 401 are performed more efficiently. In the present embodiment, the air guide grooves 440, as shown in FIGS. 15A to 15E, are fouled as W-shaped projecting grooves extending in the substantially vertical direction from the end part of the extraction solution inflow port 431 of the guiding member 302 to the top end of the guiding member holding part 435. Four are provided at constant intervals in the peripheral direction. Further, the air guide grooves 440 are provided at positions at which grooves do not continue with the air circulation grooves 439 formed at the guiding member holding part 435. The widths of the clearances of the grooves are designed so as to enable the air guide grooves 440 to substantially circulate only air through the small clearances fouled between the W-shaped grooves. Specifically, the widths of the clearances of the air guide grooves 440 through which the air circulates are preferably 0.05 mm to 0.15 mm, more preferably 0.08 mm to 0.12 mm. Due to the air guide grooves 440, the air flowing from the extraction solution outflow port 432 side through the air circulation grooves 439 flows through the air guide grooves 440 to the extraction solution inflow port 331 side and circulates to the extraction solution guide 433. Due to this, the extraction solution 6 smoothly moves through the extraction solution guide 433 to the detecting means 401. Note that, the air guide grooves 440 may be any structures so long as structures not allowing drops of the extraction solution 6 to enter the clearances between the guide grooves and substantially allowing flow of only air. For example, in a plane view, substantially polygonal shapes, substantially circular shapes, substantially fan shapes, or indefinite shaped grooves or pluralities of ribs etc. may be mentioned.

Further, in the present embodiment, as shown in FIG. 15D, the extraction solution outflow port 432 of the guiding member 302 is provided with outflow port side grooves 432b for reliably taking in air at the inside of the tube of the extraction member 302 when making the guiding member 302 and detecting means 401 engage. Due to this, at the time of use, air is reliably fed to the inside of the tube of the extraction member 302, air is fed to the extraction solution guide 433, and the pressure inside the extraction solution guide 433 etc. are adjusted, so absorption by the extraction solution guide 433 of the extraction solution 6 and movement of the extraction solution 6 to the detecting means 401 can be performed efficiently. In the present embodiment, the outflow port side grooves 432b are formed as recessed grooves formed at the bottom surface of the end part of the extraction solution outflow port 432 of the guiding member 302. Four recessed grooves are provided at constant intervals on the bottom surface of the end part of the extraction solution outflow port 432. The depth of the recessed grooves formed need only be a depth enabling the inflow of air. In the present embodiment, it is formed as 0.25 mm.

Next, based on FIG. 16, the testing means 401 will be explained. The testing means 401 has a configuration similar to the testing means 401 according to the fourth embodiment. In the present embodiment, the extraction solution outflow port 432 of the guiding member 302 is provided with an outflow port side groove 432b, so when making the detecting means 401 and the guiding member 302 engage, a clearance can be reliably formed enabling the flow of air between the guiding member support part 343b of the detecting means 401 and the extraction solution outflow port 432 side of the guiding member 302. For this reason, air stably flows through the slits 343d and addition hole side grooves 343e of the detecting means 401 to the extraction solution outflow port 432 of the guiding member 302. The inflowing air is supplied through the air circulation grooves 439 to the extraction solution guide 433 or flows through the air guide grooves 440 to the extraction solution inflow port 431 side. Due to this, the extraction solution 6 smoothly moves through the extraction solution guide 433 to the detecting means 401.

The rest of the explanation regarding the configuration of the guiding member 302 is similar to the case of the above-mentioned first embodiment. The functions and actions and effects are also similar. Further, the rest of the explanation of the testing means 401 is similar to the case of the above-mentioned fourth embodiment. The functions and actions and effects are also similar. Further, the configurations of the extraction container 2 and specimen sampler 5 forming the test device 102 are also similar to the case of the above-mentioned first embodiment. The functions and actions and effects are also similar.

EXAMPLES

Below, examples will be used to explain the present invention in detail.

In the following working examples and comparative examples, as the test strip of the testing means, the test strip 341 of the lateral flow type utilizing immunochromatography of the structure shown in FIG. 17 combined with the structure of the test strip 341 used in the testing means 401 shown in FIG. 16 was used. Specifically, a test strip (width 4 mm×length 77 mm), as shown in FIG. 17, was prepared by superposing various sheets forming the test strip on a baking sheet BS (width 4 mm×length 77 mm, GL-187, product made by Rohmann) to form predetermined positions. As the sheets, a sample pad 341a (width 4 mm×length 35 mm, GFDX203000, product made by Merck Millipore), a conjugate pad 341b (width 4 mm×length 10 mm, GFDX203000, product made by Merck Millipore), a membrane 341c (width 4 mm×length 25 mm, Nitrocellulose Membrane HF180, product made by Merck Millipore), and an absorption pad 341d (width 4 mm×length 25 mm, Whatman Filter Paper 740-E, product of GE Healthcare Bioscience) were used. The addition position S of the test solution or extraction solution is positioned 10 mm from one end of the test strip. The control line CL was provided at the membrane 341c so that the distance from that addition position S to the control line CL became 36 mm. The control line CL was formed by coating a goat anti-mouse IgG antibody (product of Fitzgerald Industries) on a membrane 341c in a line. Further, as the conjugate pad 341b, one on which a gold colloid labeled antibody using gold colloid (diameter 60 nm, product of BB International, EM.GC60) to label an influenza IgG mouse antibody (product of Fitzgerald Industries) in advance was used.

Example 1

Figure 16:
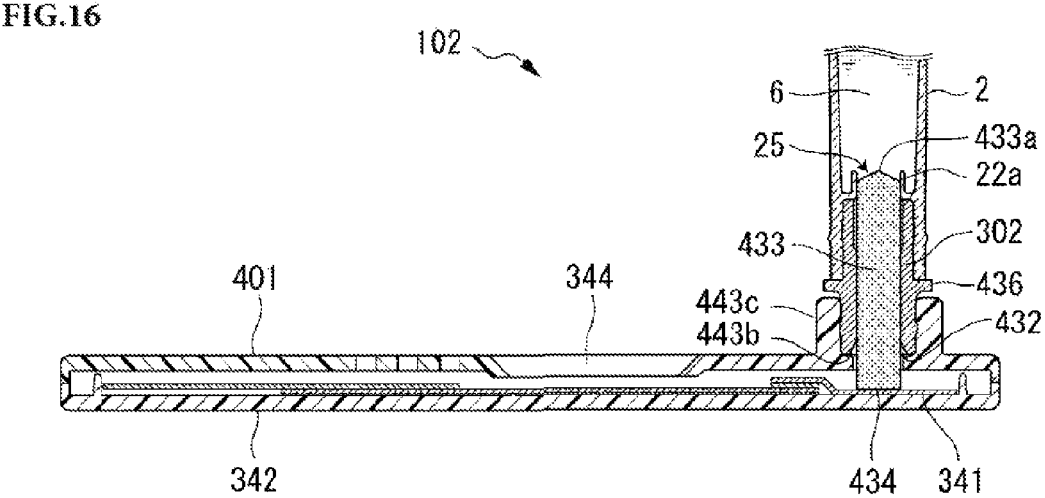
FIG. 16 is an explanatory view schematically showing the state of use of a test device according to a fifth embodiment of the present invention.
Figure 17:
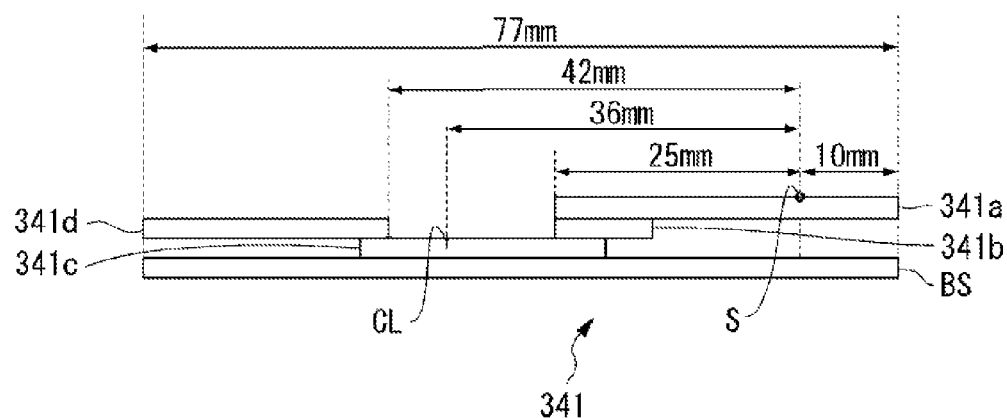
FIG. 17 is an explanatory view showing the structure of a test strip of a testing means used in the working examples and comparative examples.

The following test was performed using the test device 102 shown in FIG. 16. 350 μl of a 50 mM Tris-HCl buffer solution (pH 7.5) was added to the extraction container 2. The specimen sampling part 51 of the specimen sampler 5 shown in FIG. 1 was used to obtain the specimen shown in the following Table 1 and was placed in the extraction container 2 together with the shaft part 52 of the specimen sampler 5 as shown in FIG. 2, then the specimen sampling part 52 sampling the specimen was immersed in the Tris-HCl buffer solution. A through hole was formed at the bottom part 22 of the extraction container 2 at the extraction solution guide 433 of the guiding member 302, and an extraction solution was added to the test strip 341 of the testing means 401 through the extraction solution guide 433. As the extraction solution guide 433, a fiber bundle structure mainly comprised of polyester fiber (porosity 43%, diameter 3.5 mm×length 25 mm, ENKR-14-243, product made by Essentra Porous Technologies) was used. Note that, the specimens of Test Nos. 2 to 4 were specimens of nasal discharge sampled from two subjects right before the tests. Test No. 3 sampled the same specimen as in Test No. 2 by a specimen sampler two times to raise the specimen concentration. Further, the specimens of Test Nos. 5 to 7 were commercially available nasal discharge specimens, but had lower viscosities compared with the specimens of Test Nos. 2 to 4. The time from right after addition of the extraction solution to when the control line CL on the test strip began to become visible, that is, the time until the extraction solution added to the addition position S reached the control line CL, was measured. The results are shown in the following Table 1.

TABLE 1

| Test No. | Specimen | Time until CL started to be visible (sec) |
|---|---|---|
| 1 | None (only Tris-HCl buffer) | 47 |
| 2 | Nasal discharge viscous specimen A | 46 |
| 3 | Nasal discharge viscous specimen A (2 samplings) | 95 |
| 4 | Nasal discharge viscous specimen B | 55 |
| 5 | Nasal discharge specimen 1 (BHR899) | 33 |
| 6 | Nasal discharge specimen 2 (BHR900) | 40 |
| 7 | Nasal discharge specimen 3 (BHR901) | 36 |

According to the results of the above Example 1, the time until the control line CL started to become visible became a short one of within about 1 minute regardless of the extraction solution being introduced to the test strip through the extraction solution guide. It was learned that the extraction solution was smoothly introduced to the test strip from the guiding member. Further, if comparing the buffer solution of Test No. 1 not having viscosity and the specimen extraction solutions of Test Nos. 2 to 7 having viscosity, except for Test No. 3 with a high specimen concentration and high viscosity, no large difference was seen in the time until the CL started to become visible. Further, after the end of the tests, the fiber bundle structures were taken out from the guiding members and examined, whereupon it was confirmed that viscous substances were deposited around the fiber bundle structures used in Test Nos. 2 to 4. From this, it was learned that the fiber bundle structures had the action of filtering out the viscous substance in the extraction solution while introducing the extraction solution. Further, after the end of the tests, the test strips were taken out from the testing means and examined, whereupon unlike the comparative examples shown below, overflow of the extraction solution was not observed. This is believed to be because the extraction solution guide of the guiding member has an absorption action, the excess extraction solution remains in the extraction solution guide.

Comparative Example

Figure 18:
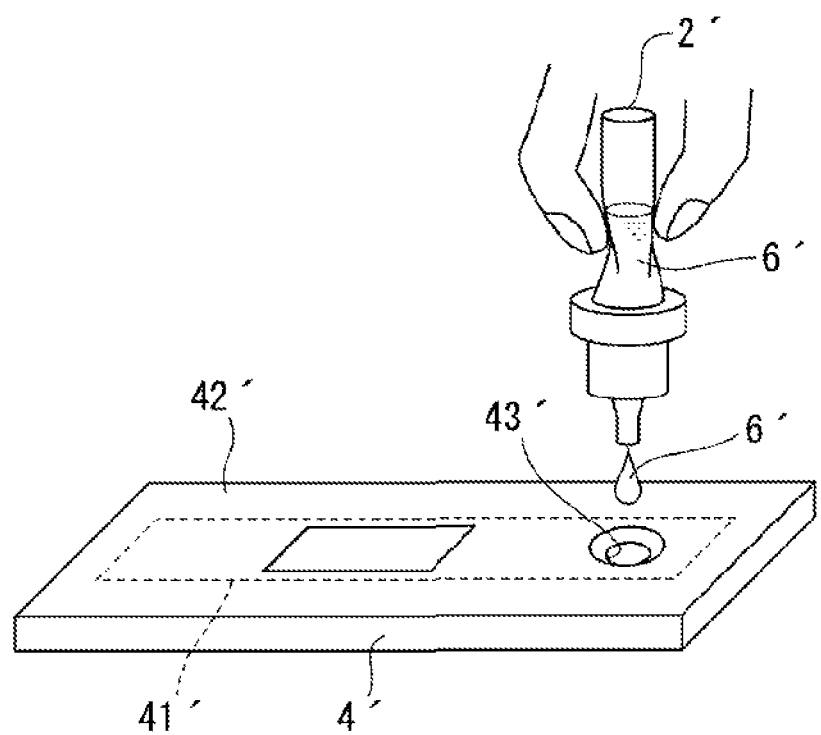
FIG. 18 is an explanatory view showing the state of use of a conventional test device.

Using the conventional test device shown in FIG. 18, the test solution shown in the following Table 2 was directly added dropwise on to the test strip of the testing means using a pipette. The time from right after the addition of the test solution to when the control line CL on the test strip started to be visible, that is, the time until the test solution added to the addition position S reached the control line CL, was measured. The results are shown in the following Table 2.

TABLE 2

| | Test solution | Amount of addition (μl) | Time until Cl started to become visible (sec) |
|---|---|---|---|
| 1 | 50 mM Tris-HCl buffer solution (pH 7.5) | 350 | 28 |

According to the results of the above comparative example, the time until the control line CL started becoming visible was within about 30 seconds. Further, when the test strip was taken out from the testing means after the end of the test, it was confirmed that excess test solution overflowed from the test strip.

Example 2

The following test was performed using the test device 102 shown in FIG. 16. The amounts of 50 mM Tris-HCl buffer solution (pH 7.5) were added to the extraction container 2 in the amounts shown in Table 3. A through hole was formed at the bottom part 22 of the extraction container 2 at the extraction solution guide 433 of the guiding member 302, and a test solution was added to the test strip 341 of the testing means 401 through the extraction solution guide 433. Note that, as the extraction solution guide 433, two types, a fiber bundle structure 1 mainly comprised of polyester fiber (porosity 43%, diameter 3.5 mm×length 25 mm, ENKR-14-243, product made by Essentra Porous Technologies) and a fiber bundle structure 2 (porosity 55%, diameter 3.5 mm×length 25 mm, ENKR-14-242, product made by Essentra Porous Technologies), were tested. The time from right after the addition of the test solution to when the control line CL on the test strip started to be visible, that is, the time until the test solution added to the addition position S reached the control line CL, was measured. Further, 5 minutes after the start of the test, the amount of the test solution remaining in the extraction container 2 was measured.

TABLE 3

| Amount of test solution | Fiber bundle structure 1 (porosity: 43%) | | Fiber bundle structure 2 (porosity: 55%) | |
|---|---|---|---|---|
| | Time until Cl started to become visible (sec) | Remaining amount in container (µl) | Time until Cl started to become visible (sec) | Remaining amount in container (µl) |
| 300 µl | 35 | 0 | 45 | 0 |
| 400 µl | 45 | 70 | 48 | 50 |
| 500 µl | 34 | 140 | 30 | 80 |

According to the results of Example 2, it was learned that the time until the control line CL started to become visible was somewhat shorter in the case of the small porosity fiber bundle structure 1. Further, in each test using each fiber bundle structure, excess test solution did not remain in the extraction container 2, test solution was not introduced exceeding the amount of absorption of the test strip, and the test solution did not overflow from the test strip. Note that, while a difference was seen in the amount of the test solution remaining in the container depending on the type of fiber bundle structure used, this was believed to be because a larger porosity caused a larger amount of solution to be able to be absorbed and held inside the fiber bundle structure.

Example 3

The following test was performed using the test device 102 shown in FIG. 16. For the test strip 341 shown in FIG. 17, test strips 341 changed in only the length of the absorption pads 341 to 20 mm, 10 mm, and 5 mm prepared and tested to confirm the amounts of test solution absorbed in the test strips 341. 400 µl of a 50 mM Tris-HCl buffer solution (pH 7.5) was added to the extraction container 2, a through hole was formed at the bottom part 22 of the extraction container 2 at the extraction solution guide 433 of the guiding member 302, and a test solution as added to the test strip 341 of the testing means 401 through the extraction solution guide 433. Note that, as the extraction solution guide 433, a fiber bundle structure mainly comprised of polyester fiber (porosity 43%, diameter 3.5 mm×length 25 mm, ENKR-14-243, product made by Essentra Porous Technologies) was used. 15 minutes after the start of the test, the test strip was measured for weight and the amount of test solution absorbed in the test strip was calculated.

TABLE 4

| | Length of absorption pad | | |
|---|---|---|---|
| | 5 mm | 10 mm | 20 mm |
| Amount of absorption (mg) | 126 | 135 | 158 |

According to the results of Example 3, it was confirmed that the amount of absorption of the test solution by the test strip increased in proportion to the increased length of the absorption pad. Further, in each test, excess test solution did not remain in the extraction container and test solution did not overflow from the test strip. Due to this, it was learned that by adjusting the components of the test strip, in particular the length, area, thickness, etc. of the absorption pad, it is possible to make the amount of test solution which can be introduced into the test strip substantially constant.

The present invention is not limited to the content of the above embodiments and examples. Various design changes within the scope not deviating from the gist of the invention described in the claims are included within its technical scope.

REFERENCE SIGNS LIST 1, 10, 100, 101, 102: test device
2, 20, 200, 2': extraction container
21, 121, 221: barrel part
21a: inside wall
21b: outside wall
22, 122, 222: bottom part
22a, 122a, 222a: sealing part
22b, 122b: holding region
22c, 122c: bottom part side engaging part
22d, 122d: end part
22e, 122f: breaking part
23, 223: open part
223a: open part side engaging part
23b: open part side sealing part
24: lid member
25, 125: through hole
3, 30, 300, 301, 302: guiding member
31, 131, 231, 331, 431: extraction solution inflow port
31a, 131a, 231a, 331a, 431a: inflow port side engaging part
131b: projecting tab part
32, 132, 232, 332, 432: extraction solution outflow port
32a, 132a, 232a, 332a, 432a: outflow port side engaging part
432b: outflow port side groove
33, 133, 233, 333, 433: extraction solution guide
33a, 433a: pointed end part
33b, 133b, 233b, 333b, 433b: outflow port side end part
34, 134, 234, 334, 434: projecting part
35, 135, 235, 335, 435: guide holding part
36, 136, 236, 336, 436: flange part
337, 437: guide support part
338, 438: clearance
339, 439: air circulation groove
440: air guide groove
L33: length of extraction solution guide
4, 40, 400, 401, 4': testing means
41, 141, 241, 341, 41': test strip
41a, 141a, 241a, 341a: sample pad
41b, 141b, 241b, 341b: conjugate pad
41c, 141c, 241c, 341c: membrane
41d, 341d: absorption pad
42, 142, 242, 342, 42': housing
43, 143, 243, 343, 43': addition hole
43a, 143a, 243a, 343a: addition hole side engaging part
43b, 143b, 243b, 343b: guiding member support part
43c, 143c, 243c, 343c: addition hole wall
343d: slit
343e: addition hole side groove
44, 344: judging window
5: specimen sampler
51: specimen sampling part
52: shaft part
52a: pliable part
52b: base part
53: notch
54: cap part
54a: cap sealing part
6, 6': extraction solution

The invention claimed is:

1. A test device comprising:
an extraction container containing an extraction solution, the extraction container having a barrel part and a bottom part, the bottom part having a sealing part configured to be openable;
a tubular guiding member having an extraction solution inflow port on one end, an extraction solution outflow port on another end, and a rod-shaped extraction solution guide slidably engaged within the tubular guiding member, the rod-shaped extraction solution guide having a projecting part projecting beyond the extraction solution outflow port; and
a test housing having an addition hole and a test strip,
wherein the extraction solution inflow port of the tubular guiding member is fitted into the bottom part of the extraction container in a sealed manner, the extraction solution outflow port of the tubular guiding member is fitted into the addition hole of the test housing, the projecting part of the rod-shaped extraction solution guide abuts against the test strip, the sealing part is opened, and the rod-shaped extraction solution guide draws the extraction solution from the extraction container onto the test strip that tests the extraction solution utilizing immunochromatography or nucleic acid chromatography.

2. The test device according to claim 1, wherein the rod-shaped extraction solution guide has a point that opens the sealing part when the extraction solution inflow port of the tubular guiding member is fitted into the bottom part of the extraction container.

3. The test device according to claim 1, wherein the extraction solution inflow port of the tubular guiding member has a projecting tab part that opens the sealing part when the extraction solution inflow port of the tubular guiding member is fitted into the bottom part of the extraction container.

4. The test device according to claim 1, wherein the tubular guiding member further includes an inside wall and a guide holding part projecting from the inside wall in a peripheral direction, the guide holding part engaging the rod-shaped extraction solution guide in a slidable manner.

5. The test device according to claim 4, wherein the guide holding part includes an air circulation groove extending axially adjacent the rod-shaped extraction solution guide.

6. The test device according to claim 5, wherein the air circulation groove has a width of 0.15 mm to 0.25 mm.

7. The test device according to claim 1, wherein the extraction solution inflow port of the tubular guiding member has an inflow port side engaging part that engages an inside wall of the bottom part of the extraction container when the extraction solution inflow port of the tubular guiding member is fitted into the bottom part of the extraction container.

8. The test device according to claim 1, wherein the extraction solution outflow port of the tubular guiding member has an outflow port side engaging part that engages an inside wall of the addition hole of the test housing when the extraction solution outflow port of the tubular guiding member is fitted into the addition hole of the test housing.

9. The test device according claim 1, wherein the extraction container is made of a rigid material.

10. The test device according to claim 1, wherein the rod-shaped extraction solution guide is a fiber bundle structure.

11. The test device according to claim 1, wherein the rod-shaped extraction solution guide is a porous body.

* * * * *